United States Patent
Wisnoskey et al.

(10) Patent No.: US 10,967,189 B2
(45) Date of Patent: *Apr. 6, 2021

(54) METHODS AND SYSTEMS FOR SELECTIVELY DELIVERING DIFFERENT TYPES OF BI-VENTRICULAR PACING

(71) Applicant: Pacesetter, Inc., Santa Clara, CA (US)

(72) Inventors: Brian Wisnoskey, Cuyahoga, OH (US); Yelena Nabutovsky, Mountain View, CA (US); Jennifer Rhude, Carbondale, IL (US); Gary Cranke, Madison, OH (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/204,033

(22) Filed: Nov. 29, 2018

(65) Prior Publication Data

US 2019/0091478 A1    Mar. 28, 2019

Related U.S. Application Data

(62) Division of application No. 15/251,524, filed on Aug. 30, 2016, now Pat. No. 10,173,066.

(51) Int. Cl.
*A61N 1/365* (2006.01)
*A61N 1/368* (2006.01)

(52) U.S. Cl.
CPC ..... *A61N 1/36585* (2013.01); *A61N 1/36564* (2013.01); *A61N 1/36843* (2017.08)

(58) Field of Classification Search
CPC ............ A61N 1/36585; A61N 1/36843; A61N 1/36564

See application file for complete search history.

(56) References Cited

U.S. PATENT DOCUMENTS

| | | |
|---|---|---|
| 7,181,284 B2 | 2/2007 | Burns et al. |
| 7,546,161 B1 | 6/2009 | Bjorling et al. |

(Continued)

FOREIGN PATENT DOCUMENTS

WO    WO 1999/010042 A1    3/1999

OTHER PUBLICATIONS

Restriction Requirement dated Jul. 18, 2018; Parent U.S. Appl. No. 15/251,524.

(Continued)

*Primary Examiner* — Rex R Holmes
(74) *Attorney, Agent, or Firm* — Vierra Magen Marcus LLP

(57) ABSTRACT

Baseline BiV pacing is delivered and a corresponding baseline BiV efficacy score is determined. Intrinsic AV conduction is allowed and an intrinsic AV conduction interval is determined. BiV fusion pacing is delivered and a corresponding efficacy score is determined, for each of a plurality of different paced AV delays, each determined based on the intrinsic AV conduction interval and a different negative hysteresis delta. The baseline BiV pacing is selected for delivery during a period of time if the baseline BiV efficacy score is better than all of the efficacy scores. BiV fusion pacing is selected for delivery during the period of time, using one of the plurality of different paced AV delays for which a corresponding efficacy score was determined, if the efficacy score corresponding to at least one of the plurality of different paced AV delays is better than the baseline BiV efficacy score.

20 Claims, 8 Drawing Sheets

(56) References Cited

U.S. PATENT DOCUMENTS

| | | |
|---|---|---|
| 7,778,706 B1 | 8/2010 | Min |
| 7,941,217 B1 | 5/2011 | Pei et al. |
| 8,116,866 B2 | 2/2012 | Yonce et al. |
| 8,175,707 B1 | 5/2012 | Wright et al. |
| 8,229,557 B2 | 7/2012 | Patangay et al. |
| 8,353,841 B2 | 1/2013 | White et al. |
| 8,442,634 B2 | 5/2013 | Min et al. |
| 8,600,487 B2 | 12/2013 | Soriano et al. |
| 8,700,149 B2 | 4/2014 | Patangay et al. |
| 8,718,750 B2 | 5/2014 | Lian et al. |
| 9,254,391 B2 | 2/2016 | Ryu et al. |
| 9,272,147 B2 | 3/2016 | Prakash et al. |
| 2003/0004548 A1* | 1/2003 | Warkentin ............ A61N 1/3627 607/9 |
| 2006/0149328 A1 | 7/2006 | Parikh et al. |
| 2006/0155338 A1* | 7/2006 | Mongeon ............ A61N 1/3684 607/9 |
| 2007/0191892 A1 | 8/2007 | Mullen et al. |
| 2009/0118783 A1* | 5/2009 | Patangay ............ A61N 1/36564 607/18 |
| 2009/0234411 A1 | 9/2009 | Sambelashvili et al. |
| 2010/0114232 A1 | 5/2010 | Min |
| 2014/0155769 A1 | 6/2014 | White et al. |
| 2018/0056076 A1 | 3/2018 | Wisnoskey et al. |

OTHER PUBLICATIONS

Response to Election/Restriction Requirement dated Aug. 10, 2018; Parent U.S. Appl. No. 15/251,524.

Ex Parte Quayle mailed Sep. 24, 2018; Parent U.S. Appl. No. 15/251,524.

Amendment and Response to Non-final Office Action dated Sep. 26, 2018; Parent U.S. Appl. No. 15/251,524.

Notice of Allowance dated Nov. 16, 2018; Parent U.S. Appl. No. 15/251,524.

* cited by examiner

METHODS AND SYSTEMS FOR SELECTIVELY DELIVERING DIFFERENT TYPES OF BI-VENTRICULAR PACING

PRIORITY CLAIM

This application is a Divisional of, and claims priority to, U.S. patent application Ser. No. 15/251,524, filed Aug. 30, 2016, which issued as U.S. Pat. No. 10,173,066 on Jan. 8, 2019, which is incorporated herein by reference.

RELATED APPLICATIONS

This application is related to commonly assigned U.S. patent application Ser. No. 15/015,031, filed Feb. 3, 2016, which is incorporated herein by reference.

TECHNICAL FIELD

Embodiments of the present technology generally relate to methods and systems that provide for automatic, adaptive, and programmable bi-ventricular pacing, and select among different types of bi-ventricular pacing.

BACKGROUND OF THE INVENTION

Implantable stimulation devices or cardiac pacemakers are a class of cardiac rhythm management devices that provide electrical stimulation in the form of pacing pulses to selected chambers of the heart. As the term is used herein, a pacemaker is any cardiac rhythm management device with a pacing functionality regardless of any additional functions it may perform, such as cardioversion/defibrillation.

A pacemaker is comprised of two major components, a pulse generator and a lead. The pulse generator generates the pacing stimulation pulses and includes the electronic circuitry and the power cell or battery. The lead, or leads, is implanted within the heart and has electrodes which electrically couples the pacemaker to the desired heart chamber(s). A lead may provide both unipolar and bipolar pacing and/or sensing configurations. In the unipolar configuration, the pacing pulses are generally applied (or responses are sensed) between an electrode carried by the lead and a case of the pulse generator or an electrode of another lead within the heart. In the bipolar configuration, the pacing pulses are applied (or responses are sensed) between a pair of electrodes carried by the same lead.

When the patient's own intrinsic rhythm fails, pacemakers can deliver pacing pulses to a heart chamber to induce a depolarization of that chamber, which is followed by a mechanical contraction of that chamber. For example, the pacemaker may deliver bi-ventricular (BiV) pacing pulses to the left ventricle (LV) and right ventricle (RV) of the heart. Conventionally, BiV pacing occurs at an expiration of a fixed atrio-ventricular (AV) delay that preempts a patient's intrinsic cardiac conduction to force BiV pacing therapy. Pacemakers further include sensing circuits that sense cardiac activity for the detection of intrinsic cardiac events such as intrinsic atrial depolarizations (detectable as P waves) and intrinsic ventricular depolarizations (detectable as R waves). By monitoring cardiac activity, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart. This therapy is referred to as cardiac resynchronization therapy (CRT).

However, some patients fail to respond to conventional CRT. Existing BiV pacing techniques do not adapt to changes in patient status. Thus, it becomes important to take into account changes in a patient's intrinsic conduction time, which can affect appropriate timing of the BiV pacing pulses. For example, the intrinsic conduction time of the patient can change in response to variations in heart rate, activity level (e.g., exercise), medications, clinical status, and/or the like. Additionally, existing BiV pacing techniques are not customizable to patient-specific timing.

Patients with wide QRS duration and left bundle branch block (LBBB) typically derive the most benefit from CRT. In addition, targeting the site of latest LV electrical activation with BiV pacing has been shown to be associated with reverse ventricular remodeling and quality of life improvements. These studies implicate that LV electrical dyssynchrony plays an important role in CRT response and taken together suggest a role for correction of electrical dyssynchrony in improving response to CRT using BiV fusion pacing. BiV fusion pacing corresponds to timing the BiV pacing pulse to arrive coincident with a patient's intrinsic right bundle conduction.

While BiV fusion pacing has proven to be beneficial in certain patients, there is still room for improving BiV pacing techniques to further improve patient outcomes.

SUMMARY

Certain embodiments of the present technology are directed to methods for selectively delivering different types of bi-ventricular (BiV) pacing in dependence on efficacy scores. Each efficacy score can be, e.g., a QRS score that can be based on QRS width, overall QRS morphology, and/or the like. In general, the narrower a QRS width the better the efficacy, and the wider a QRS width the worse the efficacy. This is because a wide QRS complex (e.g., exceeding 100 milliseconds) is often associated with bundle branch block and/or some other AV conduction abnormality. Accordingly, where a QRS score (and more generally, an efficacy score) is based on QRS width, the narrower the QRS width that occurs in response to a specific type of pacing, the higher the efficacy score, assuming the higher the score the better. Where a QRS score (and more generally, an efficacy score) is based on QRS morphology, the morphology of one or more QRS complexes can be compared to a predefined and stored optimal or preferred QRS complex template, with the greater the similarity that the higher the score. Depending on the score, and more generally, depending upon implementation, the "best" score may be the one with the lowest value, or the one with the highest value. For example, where an efficacy score is the QRS width, or proportional thereto, then the best efficacy score would be the one with the lowest value. For another example, where the efficacy score is a measure of similarity to an optimal or preferred QRS morphology template, then the best efficacy score would be the one with the highest value. Alternatively, or additionally, efficacy scores can be based on one or more hemodynamic measurements obtained using one or more sensors, such as, but not limited to, an implantable sensor that measures pulmonary arterial pressure (PAP) or a surrogate thereof. Depending upon implementation, each such value can be converted to a score, which may be directly of inversely proportional to the value. It would also be possible to combine multiple measures of efficacy into a single efficacy score.

In accordance with an embodiment, a method includes delivering baseline BiV pacing for a plurality of cardiac cycles using a baseline paced atrioventricular (AV) delay and determining a corresponding baseline BiV efficacy score. The method also includes setting a paced AV delay to a value that is greater than the baseline AV delay for one or more cardiac cycles, to thereby allow for intrinsic AV conduction, and determining an intrinsic AV conduction interval. The method further includes delivering adaptive BiV fusion pacing while a negative AV hysteresis (NAVH) mode is turned on. In accordance with an embodiment, such adaptive BiV fusion pacing comprises, for each of a plurality of different paced AV delays, delivering BiV fusion pacing for a plurality of cardiac cycles and determining a corresponding NAVH efficacy score. The NAVH mode is considered to be turned "on" when an NAVH algorithm is used to specify paced AV delays, wherein an NAVH algorithm is any algorithm that determines paced AV delays based on an intrinsic AV conduction interval and negative hysteresis deltas. In other words, the NAVH mode is considered to be turned on when paced AV delays are determined based on an intrinsic AV conduction interval and negative hysteresis deltas. An exemplary NAVH algorithm is: Paced AV delay=intrinsic AV conduction interval−Negative Hysteresis Delta, which algorithm is often referred to below as Equation 1. Further, to achieve fusion, at least one of the pulses delivered during each cycle of the adaptive BiV fusion pacing is timed to be delivered concurrently with an intrinsic right ventricular conduction.

The method also includes determining whether the efficacy score corresponding to at least one of the plurality of different paced AV delays, used for delivering adaptive BiV fusion while the NAVH mode is turned on, is better than the baseline BiV efficacy score. If the NAVH efficacy score corresponding to at least one of the plurality of different paced AV delays (used for delivering adaptive BiV fusion while the NAVH mode is turned on) is not better than the baseline BiV efficacy score, then the NAVH mode is turned or left off and the baseline BiV pacing is delivered for a plurality of cardiac cycles using the baseline AV delay. If the efficacy score corresponding to at least one of the plurality of different paced AV delays (used for delivering adaptive BiV fusion while the NAVH mode is turned on) is better than the baseline BiV efficacy score, then the NAVH mode is turned or left on and BiV fusion pacing is delivered for a plurality of cardiac cycles using the paced AV delay that resulted in a best one of the NAVH efficacy scores.

In accordance with certain embodiments, a corresponding intrinsic AV conduction efficacy score is also determined. In such embodiments, the method further comprises, determining whether the intrinsic AV conduction efficacy score is better than the baseline BiV efficacy score, and better than all of the NAVH efficacy scores determined for the plurality of different paced AV delays (used for delivering adaptive BiV fusion while the NAVH mode is turned on). If the intrinsic AV conduction efficacy score is better than the baseline BiV efficacy score, and better than all of the NAVH efficacy scores determined for the plurality of different paced AV delays (used for delivering adaptive BiV fusion while the NAVH mode is turned on), then the NAVH mode is turned or left off, the baseline BiV pacing is turned or left off, and intrinsic AV conduction is allowed to occur for a plurality of cardiac cycles. Then, after allowing for intrinsic AV conduction for the plurality of cardiac cycles, the previously described steps are repeated. More generally, the above described steps can be repeated from time to time.

In accordance with certain embodiments, an activity level of a patient is monitored, and many of the above described steps are repeated each time the activity level of the patient changes beyond a threshold, or changes from one type of activity level to another type of activity level.

In accordance with certain embodiments, there is a determination whether at least one premature ventricular contraction (PVC) occurred while delivering the baseline BiV pacing, and in response to determining that at least one PVC occurred while delivering the baseline BiV pacing, the corresponding baseline BiV efficacy score is determined in a manner that is unaffected by any PVC(s). Additionally, or alternatively, there is a determination whether at least one PVC occurred while the AV delay is extended by the amount sufficient to allow for intrinsic AV conduction. In response to determining that at least one PVC occurred while the AV delay is extended by the amount sufficient to allow for intrinsic AV conduction, the intrinsic AV conduction interval is determined in a manner that is unaffected by any PVC(s). Additionally, or alternatively, there is a determination whether at least one PVC occurred while delivering the adaptive BiV fusion pacing. In response to determining that at least one PVC occurred while delivering the adaptive baseline BiV pacing, the corresponding NAVH efficacy score(s) is/are determined in a manner that is unaffected by any PVC(s).

In accordance with certain embodiments, the method also includes, for each of a plurality of different inter-ventricular (LV-RV) delays, delivering BiV pacing for a plurality of cardiac cycles and determining a corresponding LV-RV efficacy score, and selecting, for use during further BiV pacing, the one of the LV-RV delays corresponding to a best one of the LV-RV efficacy scores.

In accordance with certain embodiments, the method also includes for each of a plurality of different intra-ventricular (LV1-LV2) delays, delivering BiV pacing that includes pacing at multiple left ventricular locations for a plurality of cardiac cycles and determining a corresponding LV1-LV2 efficacy score, and selecting, for use during further BiV pacing that includes pacing at multiple left ventricular locations, the one of the LV1-LV2 delays corresponding to a best LV1-LV2 efficacy score.

Embodiments of the present technology can also be used to optimize other CRT parameters besides delays, such as, but not limited to, choice of pacing vector.

In accordance with certain embodiments, the method also includes ensuring that a delay between an atrial activation and an immediately following intrinsic ventricular activation does not exceed a specified maximum allowed AV delay by triggering ventricular pacing in response to the delay therebetween reaching the specified maximum allowed AV delay. Additionally, or alternatively, the method can include ensuring that none of the paced AV delays exceed a specified maximum allowed AV delay. In accordance with certain embodiments, the ensuring that none of the paced AV delays exceed the specified maximum allowed AV delay involves turning off the NAVH mode and returning to delivering baseline BiV pacing in response to determining that at least one of the plurality of different paced AV delays, that are each determined based on the intrinsic AV conduction interval and a different negative hysteresis delta, exceeds the specified maximum allowed AV delay. Other variations are possible, as described below.

In accordance with certain embodiments, the baseline BiV efficacy score is determined using a sensor implanted in a pulmonary artery to obtain a corresponding measure of pulmonary artery pressure (PAP) while delivering baseline BiV pacing. In such embodiments, the corresponding NAVH efficacy score (that is determined for each of the plurality of different paced AV delays) can be also determined using the sensor implanted in the pulmonary artery to obtain a corresponding measure of PAP for each of the plurality of different paced AV delays. In other words, efficacy scores can be measures of PAP, or at least partially based thereon.

In accordance with certain embodiments, for each of a plurality of different sets of BiV pacing parameters, a sensor implanted in a pulmonary artery is used to obtain a corresponding measure of PAP, and one or more implanted electrodes is used to detect a QRS complex corresponding to each measure of PAP. In such embodiments, the measures of PAP can be used to select a best (e.g., lowest) one of the measures of PAP, and a QRS complex template (that corresponds to the best one of the measures of PAP) can be saved as a QRS complex template. Thereafter, the baseline BiV efficacy score can be determined by determining a measure of similarity between a QRS complex obtained while delivering the baseline BiV pacing and the saved QRS complex template that corresponds to the best one of the measures of PAP. Further, the corresponding NAVH efficacy score, that is determined for each of the plurality of different paced AV delays, can be determined by determining a corresponding measure of similarity between a QRS complex obtained while pacing using one of the different paced AV delays and the saved QRS complex template that corresponds to the best one of the measures of PAP.

A system, according to certain embodiments of the present technology, includes, inter alia, a first lead having at least one electrode configured to be implanted in a left ventricle and a second lead having at least one electrode configured to be implanted in a right ventricle. Further, the system includes at least one pulse generator, at least one sensing circuit, and at least one processor. Each of the pulse generator(s) is coupleable to at least one of the first and second leads and is configured to deliver cardiac stimulation pulses to pacing sites using at least one of the electrodes. Each of the sensing circuit(s) is configured to obtain at least one signal indicative of electrical activity of a patient's heart. The at least one processor is configured for use in specifying an AV pacing delay used for BiV pacing and specifying which of the electrodes are used for pacing. The system is configured to use the leads, the pulse generator(s), the sensing circuit(s), and the processor(s), to: deliver baseline BiV pacing and determine a corresponding baseline BiV efficacy score; allow for intrinsic AV conduction and determine an intrinsic AV conduction interval; and deliver BiV fusion pacing and determine a corresponding NAVH efficacy score, for each of a plurality of different paced AV delays, wherein each of the plurality of different paced AV delays is determined based on the intrinsic AV conduction interval and a different negative hysteresis delta. The system is also configured to use the leads, the pulse generator(s), the sensing circuit(s), and the processor(s), to: select and deliver baseline BiV pacing for a period of time if the baseline BiV efficacy score is better than all of the NAVH efficacy scores corresponding to the plurality of different paced AV delays used during adaptive BiV fusion pacing; and select and deliver BiV fusion pacing for the period of time, using one of the plurality of different paced AV delays for which the corresponding NAVH efficacy score was determined, if the NAVH efficacy score corresponding to at least one of the plurality of different paced AV delays used during adaptive BiV fusion pacing is better than the baseline BiV efficacy score.

In accordance with certain embodiments, the system is also configured to use the leads, the pulse generator(s), the sensing circuit(s), and the processor(s), to determine an intrinsic AV conduction efficacy score; and allow for intrinsic AV conduction for the period of time, if the intrinsic AV conduction efficacy score is better than the baseline BiV efficacy score and better than all of the NAVH efficacy scores determined for the plurality of different paced AV delays used during adaptive BiV fusion pacing.

In accordance with certain embodiments, the processor(s) is/are also configured to determine whether at least one PVC occurs while the baseline BiV pacing is being delivered, and in response to determining that at least one PVC occurs while the baseline BiV pacing is being delivered, determine the corresponding baseline BiV efficacy score in a manner that is unaffected by any PVC(s). Additionally, or alternatively, the processor(s) can be configured to determine whether at least one PVC occurs while allowing for intrinsic AV conduction, and in response to determining that at least one PVC occurs while allowing for intrinsic AV conduction, determine the intrinsic AV conduction interval in a manner that is unaffected by any PVC(s). Additionally, or alternatively, the processor(s) can be configured to determine whether at least one PVC occurs while the BiV fusion pacing is being delivered, and in response to determining that at least one PVC occurs while the BiV fusion pacing is being delivered, determine at least one of the corresponding NAVH efficacy scores in a manner that is unaffected by any PVC(s).

In accordance with certain embodiments, the system also includes a sensor configured to be implanted in a pulmonary artery. In such embodiments, the processor(s) can also be configured to determine the corresponding baseline BiV efficacy score by using the sensor to obtain a corresponding measure of PAP while baseline BiV pacing is being delivered; and determine the corresponding NAVH efficacy score, for each of the plurality of different paced AV delays, by using the sensor to obtain a corresponding measure of PAP for each of the plurality of different paced AV delays.

This summary is not intended to be a complete description of the invention. Other features and advantages of the invention will appear from the following description in which the preferred embodiments have been set forth in detail, in conjunction with the accompanying drawings and claims.

DETAILED DESCRIPTION

Figure 1:
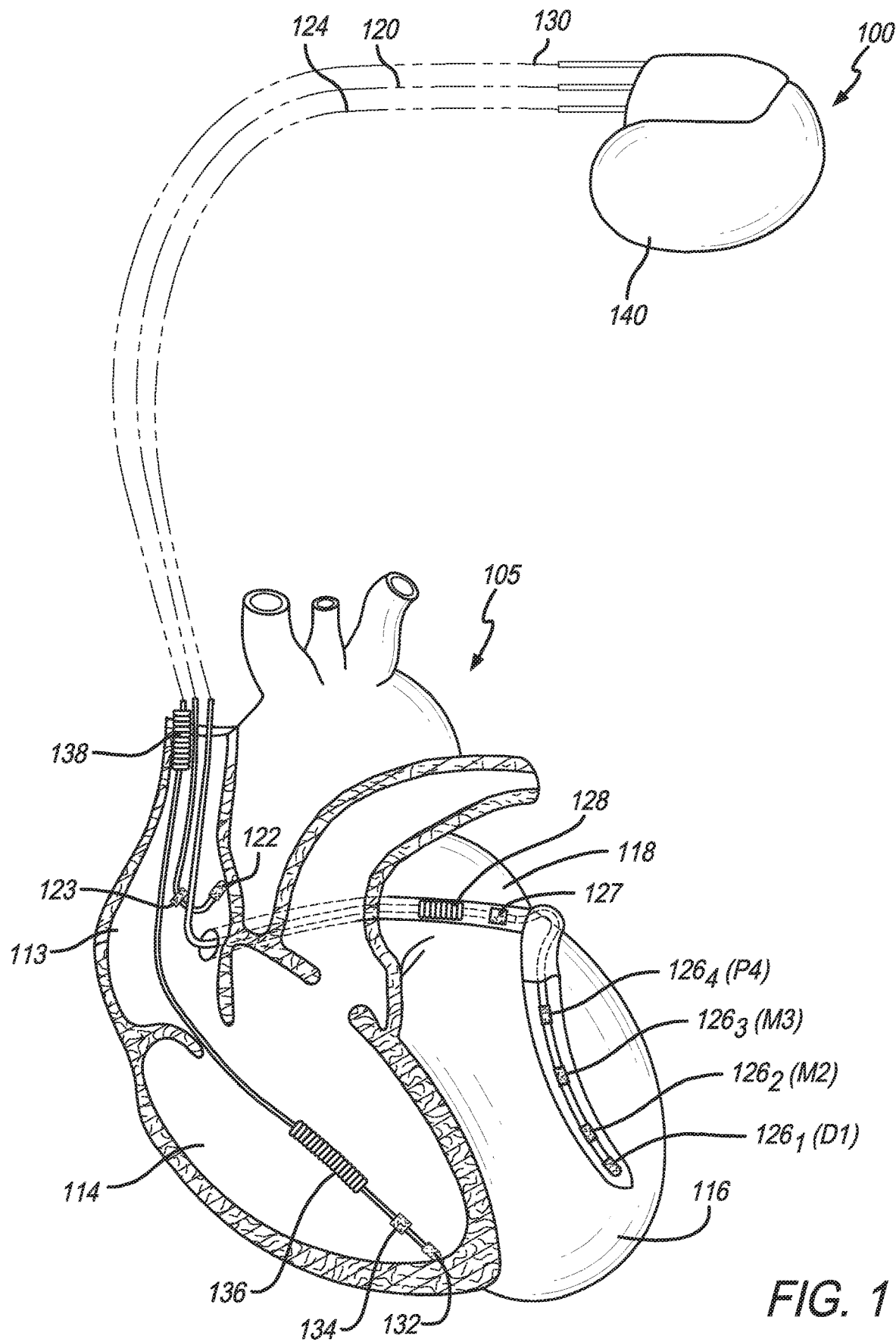
FIG. 1 illustrates an implantable medical device (IMD) in electrical communication with multiple leads implanted into a patient's heart for delivering multi-chamber stimulation and sensing cardiac activity, according to an embodiment.

The systems described herein can include or represent hardware and associated instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like (collectively "processors"). These devices may be off-the-shelf devices that perform the operations described herein from the instructions described above. Additionally or alternatively, one or more of these devices may be hard-wired with logic circuits to perform these operations.

The foregoing summary, as well as the following detailed description of certain embodiments, will be better understood when read in conjunction with the appended drawings. To the extent that the FIGS. illustrate diagrams of the functional blocks of various embodiments, the functional blocks are not necessarily indicative of the division between hardware and circuitry. Thus, for example, one or more of the functional blocks (e.g., processors or memories) may be implemented in a single piece of hardware (e.g., a general purpose signal processor, microcontroller, random access memory, hard disk, and/or the like). Similarly, the programs may be standalone programs, may be incorporated as subroutines in an operating system, may be functions in an installed imaging software package, and the like. Furthermore, to the extent that the FIGS. illustrate flow diagrams of processes of various embodiments, the operations may be described by adding, rearranging, combining, or omitting the illustrated operations without departing from the scope of the processes as described herein. It should be understood that the various embodiments are not limited to the arrangements and instrumentality shown in the drawings.

One or more embodiments generally relate to implantable medical devices (IMDs) and systems such as pacemakers and implantable cardioverter-defibrillators that provide adaptive rate BiV fusion pacing. At least one technical effect of various embodiments described herein if to continually re-assess the intrinsic conduction of the patient and modify the timing of the BiV fusion pacing in a rate-adaptive fashion. BiV fusion pacing corresponds to BiV pacing stimuli that are timed to be delivered concurrently with the intrinsic right ventricular activation of the patient.

In accordance with certain embodiments herein, methods and systems periodically or continually measure an intrinsic AV conduction interval of a patient to identify any changes due to heart rate, activity level, cardiac conduction status, and/or the like of the patient. The BiV fusion pacing may be adjusted based on the measured AV conduction interval and a negative hysteresis algorithm, which may be configured by a user (e.g., clinician, doctor, medical technician). For example, the user may define parameters of the negative hysteresis algorithm during implantation and/or medical examination of the IMD based on echocardiography (ECHO) optimization, measurement of the QRS complex, and/or the like. Based on the programmable parameters, the negative hysteresis algorithm modifies the timing of ventricular pacing to achieve fusion by setting a rate-responsive AV delay to match or "fuse" the intrinsic cardiac conduction of the patient and the ventricular activation. In at least one embodiment, the Negative Hysteresis algorithm may set an interventricular pacing delay between the left ventricle (LV) and the right ventricle (RV). Because the Negative Hysteresis algorithm is used to adjust or specify AV delays, the Negative Hysteresis algorithm can also be referred to more specifically as the Negative AV Hysteresis (NAVH) algorithm. When the NAVH algorithm is used to specify paced AV delays, a NAVH mode can be said to be turned on; and when the NAVH algorithm is not being used to specify paced AV delays, the NAVH mode can be said to be turned off.

FIG. 1 illustrates an implantable medical device (IMD) 100 in electrical communication with multiple leads implanted into a patient's heart 105 for delivering multi-chamber stimulation and sensing cardiac activity according to an embodiment. The IMD 100 may be a dual-chamber stimulation device, including an IMD, capable of treating both fast and slow arrhythmias with stimulation therapy, including cardioversion, defibrillation, and pacing stimulation, including cardiac resynchronization therapy (CRT). Optionally, the IMD 100 may be configured for single site or multi-site left ventricular (MSLV) pacing, which provides pacing pulses at more than one site within the LV chamber each pacing cycle. To provide atrial chamber pacing stimulation and sensing, the IMD 100 is shown in electrical communication with a heart 105 by way of a right atrial (RA) lead 120 having an atrial tip electrode 122 and an atrial ring electrode 123 implanted in the atrial appendage 113. The IMD 100 is also in electrical communication with the heart 105 by way of a right ventricular (RV) lead 130 having, in this embodiment, a ventricular tip electrode 132, an RV ring electrode 134, an RV coil electrode 136, and a superior vena cava (SVC) coil electrode 138. The RV lead 130 is transvenously inserted into the heart 105 so as to place the RV coil electrode 136 in the RV apex, and the SVC coil electrode 138 in the superior vena cava. Accordingly, the RV lead 130 is capable of receiving cardiac signals and delivering stimulation in the form of pacing and/or shock therapy to the right ventricle 114 (also referred to as the RV chamber).

To sense right atrial and ventricular cardiac signals and to provide left ventricle 116 (e.g., left chamber) pacing therapy, the IMD 100 is coupled to a multi-pole LV lead 124 designed for placement in various locations such as the "CS region", the epicardial space, etc. As used herein, the phrase "CS region" refers to the venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus. In an embodiment, an LV lead 124 is designed to receive atrial and ventricular cardiac signals and to deliver left ventricular pacing therapy using a set of multiple LV electrodes 126 that includes electrodes $126_1$, $126_2$, $126_3$, and $126_4$ (thereby providing a multipolar or multi-pole lead). The LV lead 124 also may deliver left atrial pacing therapy using at least an LA ring electrode 127 and shocking therapy using at least an LA coil electrode 128. In alternate embodiments, the LV lead 124 includes the LV electrodes $126_1$, $126_2$, $126_3$, and $126_4$, but does not include the LA electrodes 127 and 128. The LV lead 124 may be, for example, the Quartet™ LV pacing lead developed by St. Jude Medical Inc. (headquartered in St. Paul, Minn.), which includes four pacing electrodes on the LV lead. Although three leads 120, 124, and 130 are shown in FIG. 1, fewer or additional leads with various numbers of pacing, sensing, and/or shocking electrodes may optionally be used. For example, the LV lead 124 may have more or less than four LV electrodes 126.

When selecting a target venous branch for the LV lead 124, several factors may be taken into account. For example, it may be desirable to maximize the LV mass that may be captured by the LV lead 124. Accordingly, to maximize LV mass exposure, certain venous branches may be preferred for positioning the LV lead 124. Further, a diameter and trajectory of the venous branch is also considered to ensure that the venous branch will support chronic stability of an LV lead 124. Passive fixation of the LV lead 124 may be established through the anatomy of the host venous branch which causes the LV lead 124 to extend the distal portion thereof in a manner that differs from the LV lead's pre-formed shape. Optionally, additional factors to be considered when placing the LV lead 124 may include reducing myocardial capture thresholds, avoiding atrial and phrenic nerve stimulation, targeting site of latest LV electrical activation, and/or the like. After the LV lead 124 is positioned, the LV pacing vectors may be selected.

The LV electrode $126_1$ (also referred to as D1) is shown as being the most "distal" LV electrode with reference to how far the electrode is from the left atrium 118. The LV electrode $126_4$ (also referred to as P4) is shown as being the most "proximal" LV electrode 126 to the left atrium 118. The LV electrodes $126_2$ and $126_3$ are shown as being "middle" LV electrodes (also referred to as M2 and M3), between the distal and proximal LV electrodes $126_1$ and $126_4$, respectively. Accordingly, so as to more aptly describe their relative locations, the LV electrodes $126_1$, $126_2$, $126_3$, and $126_4$ may be referred to respectively as electrodes D1, M2, M3, and P4 (where "D" stands for "distal", "M" stands for "middle", and "P" stands from "proximal", and the numbers are arranged from most distal to most proximal, as shown in FIG. 1). Optionally, more or fewer LV electrodes may be provided on the lead 124 than the four LV electrodes D1, M2, M3, and P4.

The LV electrodes 126 are configured such that each electrode may be utilized to deliver pacing pulses and/or sense pacing pulses (e.g., monitor the response of the LV tissue to a pacing pulse). In a pacing vector or a sensing vector, each LV electrode 126 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 105 or located externally to the heart 105 (e.g., on a housing/case device 140). For example, the housing/case 140 may be referred to as the CAN and function as an anode in unipolar pacing and/or sensing vectors. The RV coil 136 may also function as an anode in unipolar pacing and/or sensing vectors. The LV electrodes 126 may be used to provide various different vectors. Some of the vectors are intraventricular LV vectors (e.g., vectors between two of the LV electrodes 126), while other vectors are interventricular vectors (e.g. vectors between an LV electrode 126 and the RV coil 136 or another electrode remote from the left ventricle 116). Below is a list of exemplary bipolar sensing vectors with LV cathodes that may be used for sensing using the LV electrodes D1, M2, M3, and P4 and the RV coil 136. In the following list, the electrode to the left of the arrow is assumed to be the cathode, and the electrode to the right of the arrow is assumed to be the anode:

D1→RV coil
M2→RV coil
M3→RV coil
P4→RV coil
D1→M2
D1→P4
M2→P4
M3→M2
M3→P4
P4→M2

It is recognized that various other types of leads and IMDs may be used with various other types of electrodes and combinations of electrodes. The foregoing electrode types/combinations are provided as non-limiting examples. Further, it is recognized that utilizing an RV coil electrode as an anode is merely one example. Various other electrodes may be configured as the anode electrode. Below is a list of exemplary bipolar pacing vectors with LV cathodes that may be used for pacing using the LV electrodes D1, M2, M3, and P4 and the RV coil 136. In the following list, the electrodes to the left of the arrow are assumed to be cathodes, and the electrode to the right of the arrow is assumed to be the anode:

D1→RV coil (or CAN)+M2→RV coil (or CAN)
M2→RV coil (or CAN)+M3→RV coil (or CAN)
M3→RV coil (or CAN)+M4→RV coil (or CAN)
M2→RV coil (or CAN)+M3→RV coil (or CAN)+ P4→RV coil (or CAN)
D1→RV coil (or CAN)+M2→RV coil (or CAN)+ M3→RV coil (or CAN)

It is noted that the preceding list is only a subset of the available pacing and sensing vectors for use with the IMD 100. Further, when delivering a series of pacing pulses, one of the above pacing vectors is used for at least the first pacing pulse in the series. Other pacing vectors may be used for subsequent pulses in the series of pacing pulses. Furthermore, additional pacing pulses may be generated in other chambers of the heart, such as the right ventricle.

Figure 2:
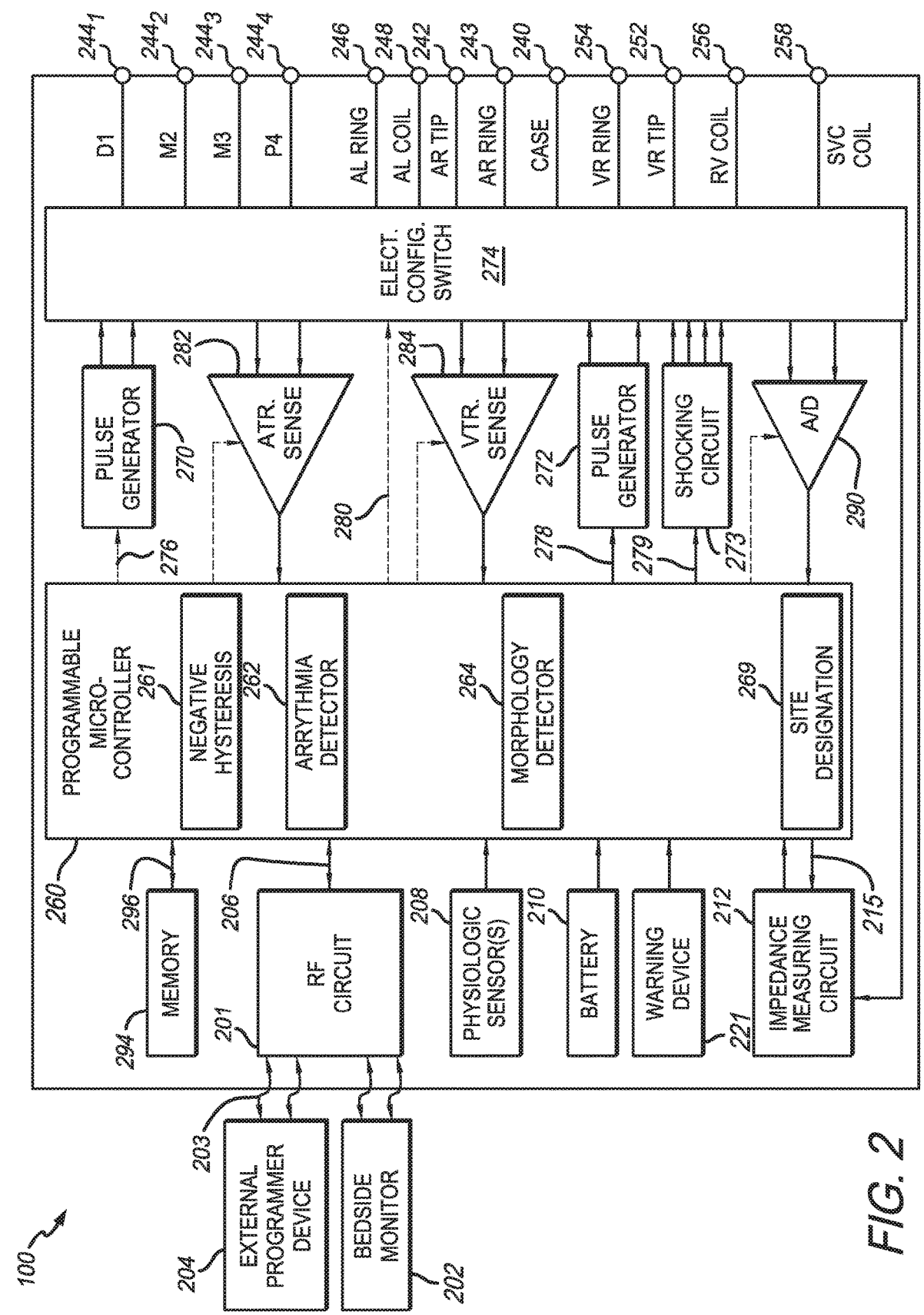
FIG. 2 illustrates a simplified block diagram of internal components of the IMD shown in FIG. 1, according to an embodiment.

FIG. 2 illustrates a simplified block diagram of internal components of the IMD 100 according to an embodiment. While a particular IMD 100 is shown, it is for illustration purposes only. One of skill in the art could readily duplicate, eliminate, or disable the appropriate circuitry in any desired combination to provide a device capable of treating the appropriate chamber(s) with cardioversion, defibrillation, and pacing stimulation. The housing/CAN 240 for IMD 100, shown schematically in FIG. 2 may be programmably selected to act as the anode for at least some unipolar modes. The CAN 240 may further be used as a return electrode alone or in combination with one or more of the coil electrodes 128, 136, and 138 (all shown in FIG. 1) for shocking purposes.

The IMD 100 further includes a connector (not shown) having a plurality of terminals, 242, 243, 244$_1$-244$_4$, 246, 248, 252, 254, 256, and 258 (shown schematically and, for convenience, with the names of the electrodes to which they are connected). As such, to achieve right atrial (RA) sensing and pacing, the connector includes at least an RA tip terminal ($A_R$ TIP) 242 adapted for connection to the atrial tip electrode 122 (shown in FIG. 1) and an RA ring ($A_R$ RING) electrode 243 adapted for connection to the RA ring electrode 123 (shown in FIG. 1). To achieve left chamber sensing, pacing, and shocking, the connector includes an LV tip terminal 244$_1$ adapted for connection to the D1 electrode and additional LV electrode terminals 244$_2$, 244$_3$, and 244$_4$ adapted for connection to the M2, M3, and P4 electrodes, respectively, of the quadripolar LV lead 124 (shown in FIG. 1). The connector also includes an LA ring terminal ($A_L$ RING) 246 and an LA shocking terminal ($A_L$ COIL) 248, which are adapted for connection to the LA ring electrode 127 (shown in FIG. 1) and the LA coil electrode 128 (shown in FIG. 1), respectively. To support right chamber sensing, pacing, and shocking, the connector further includes an RV tip terminal ($V_R$ TIP) 252, an RV ring terminal ($V_R$ RING) 254, an RV coil terminal (RV COIL) 256, and an SVC coil terminal (SVC COIL) 258, which are adapted for connection to the RV tip electrode 132, the RV ring electrode 134, the RV coil electrode 136, and the SVC coil electrode 138 (all four electrodes shown in FIG. 1), respectively.

At the core of the IMD 100 is a controller circuit 260, which controls the various modes of stimulation therapy. The controller circuit 260 (also referred to herein as a control unit or controller) may include one or more processors, a microprocessor or equivalent control circuitry, designed specifically for controlling the delivery of stimulation therapy. In at least one embodiment, the controller circuit 260 may be a microcontroller. The controller circuit 260 may further include RAM or ROM memory, logic and timing circuitry, state machine circuitry, and/or I/O circuitry. The controller circuit 260 includes the ability to process or monitor input signals (data) as controlled by a program code stored in a designated block of memory. The details of the design and operation of the controller circuit 260 are not critical to the invention. Rather, any suitable controller circuit 260 may be used that carries out the functions described herein. Among other things, the controller circuit 260 receives, processes, and manages storage of digitized cardiac data sets from the various sensors and electrodes.

A pulse generator 270 and a pulse generator 272 are configured to generate and deliver a pacing pulse from at least one RV or RA pacing site, such as at one or more pacing sites along the RA lead 120, the RV lead 130, and/or the LV lead 124 (all three leads shown in FIG. 1). For example, the pulse generator 270 generates pulses for delivery by the RA lead 120 and/or RV lead 130, while the pulse generator 272 generates pulses for delivery by the LV lead 124. The pacing pulses are routed from the pulse generators 270, 272 to selected electrodes within the leads 120, 124, 130 through an electrode configuration switch 274. It is understood that in order to provide stimulation therapy in each of the four chambers of the heart, the pulse generators 270 and 272, may include dedicated, independent pulse generators, multiplexed pulse generators, or shared pulse generators. The pulse generators 270, 272 are controlled by the controller circuit 260 via appropriate control signals 276, 278, respectively, to trigger or inhibit the stimulation pulses, including the timing and output of the pulses.

The pulse generators 270, 272 deliver, in connection with measuring the base capture threshold, successive stimulation pulses that have different stimulation amplitudes starting at an upper limit of the outer test range and decreasing by predetermined amounts. The pulse generators 270, 272 deliver, in connection with measuring the secondary capture threshold, one or more pacing pulses having stimulation amplitudes that vary over the inner test range.

Optionally, the pulse generators 270, 272 deliver one or more pacing pulses beginning with an initial stimulation amplitude having a voltage that is lower than a voltage of an initial stimulation amplitude associated with the outer test range used to measure the base capture threshold. The pulse generators 270, 272, in connection with measuring the base and secondary capture thresholds, begin at first and second outer voltages corresponding to one of the limits of the outer and inner test ranges, respectively, the first and second outer voltages differing from one another.

The electrode configuration switch 274 may include a plurality of switches for connecting the desired electrodes to the appropriate I/O circuits, thereby providing complete electrode programmability. Accordingly, the switch 274, in response to a control signal 280 from the controller circuit 260, controls the polarity of the stimulation pulses (e.g., unipolar, bipolar, etc.) by selectively actuating the appropriate combination of switches (not shown) as is known in the art. The switch 274 also switches among the various LV electrodes 226 to select the channels (e.g., vectors) to deliver and/or sense one or more of the pacing pulses. As explained herein, the switch 274 couples multiple LV electrode terminals $244_1$-$244_4$ correspond to cathodes when connected to the pulse generator 272.

Atrial sensors or sensing circuits 282 and ventricular sensors or sensing circuits 284 may also be selectively coupled to the RA lead 120, the LV lead 124, and/or the RV lead 130 (all three leads shown in FIG. 1) through the switch 274. The atrial and ventricular sensors 282 and 284 have the ability to detect the presence of cardiac activity in each of the four chambers of the heart 105 (shown in FIG. 1). For example, the atrial sensors 282 is configured to sense AV conduction of the patient. Optionally, the ventricular sensor 284 is configured to sense LV activation events at multiple LV sensing sites, such as the intrinsic cardiac conduction of the LV 116 and/or activation events generated in response to a pacing pulse.

The atrial sensing circuits 282 and ventricular sensing circuits 284 may include dedicated sense amplifiers, multiplexed amplifiers, or shared amplifiers. The switch 274 determines the "sensing polarity" or sensing vector of the cardiac signal by selectively opening and/or closing the appropriate switches, as is known in the art. In this way, a clinician may program the sensing polarity independent of the stimulation polarity. The outputs of the atrial and ventricular sensing circuits 282 and 284 are connected to the controller circuit 260. The outputs, in turn, are able to trigger or inhibit the atrial and ventricular pulse generators 270 and 272, respectively, in a demand fashion in response to the absence or presence of cardiac activity in the appropriate chambers of the heart 105. The ventricular sensing circuit 284 can be considered part of a ventricular channel, wherein the ventricular channel includes circuitry for sensing cardiac signals in one or both ventricles. The atrial sensing circuit 282 can be considered part of an atrial channel, wherein the atrial channel includes circuitry for sensing cardiac signals in one or both atrium.

Cardiac signals are also applied to the inputs of an analog-to-digital (A/D) data acquisition system 290. The A/D data acquisition system 290 is configured to acquire intracardiac electrogram (IEGM) signals, convert the raw analog data into a digital signal, and store the digital signals for later processing and/or telemetric transmission. The telemetric transmission may be to an external programmer 204, a bedside monitor, and/or a personal advisory module (PAM) 202. The data acquisition system 290 may be operatively coupled to the RA lead 120, the LV lead 124, and the RV lead 130 (all three leads shown in FIG. 1) through the switch 274 to sample cardiac signals across any pair of desired electrodes.

The controller circuit 260 controls the actual delivery of CRT pacing pulses to synchronize the contractions of the right and left ventricles. For example, the CRT pacing pulses may be BiV fusion pacing delivered by the IMD 100 concurrently and/or simultaneously with the intrinsic ventricular events of the heart 105. The controller circuit 260 controls the number, timing, and output of the CRT pacing pulses delivered during each cardiac cycle by utilizing a negative hysteresis module 261 of the controller circuit 260.

In various embodiments, the negative hysteresis module 261 may be a negative hysteresis algorithm executed by the controller circuit 260. The negative hysteresis module 261 may control the timing of the CRT pacing pulses, including, but not limited to, pacing rate, atrio-ventricular (AV) delay, interatrial conduction delay, interventricular conduction delay, and/or intraventricular pacing delay. For example, the negative hysteresis module 261 may instruct the pulse generators 270, 272 when to deliver the pacing pulses to the switch 274 for the LV 116 or the RV 114. The negative hysteresis module 265 controls the timing of the CRT pacing pulses to be delivered to the LV lead 124 concurrently and/or simultaneously with the intrinsic cardiac conduction of the RV 114, which configures the CRT pacing pulses to BiV fusion pacing. For example, in connection with FIG. 3, the negative hysteresis module 265 may time the CRT pacing pulses based on an intrinsic AV conduction interval 314 and a negative hysteresis delta.

Figure 3:
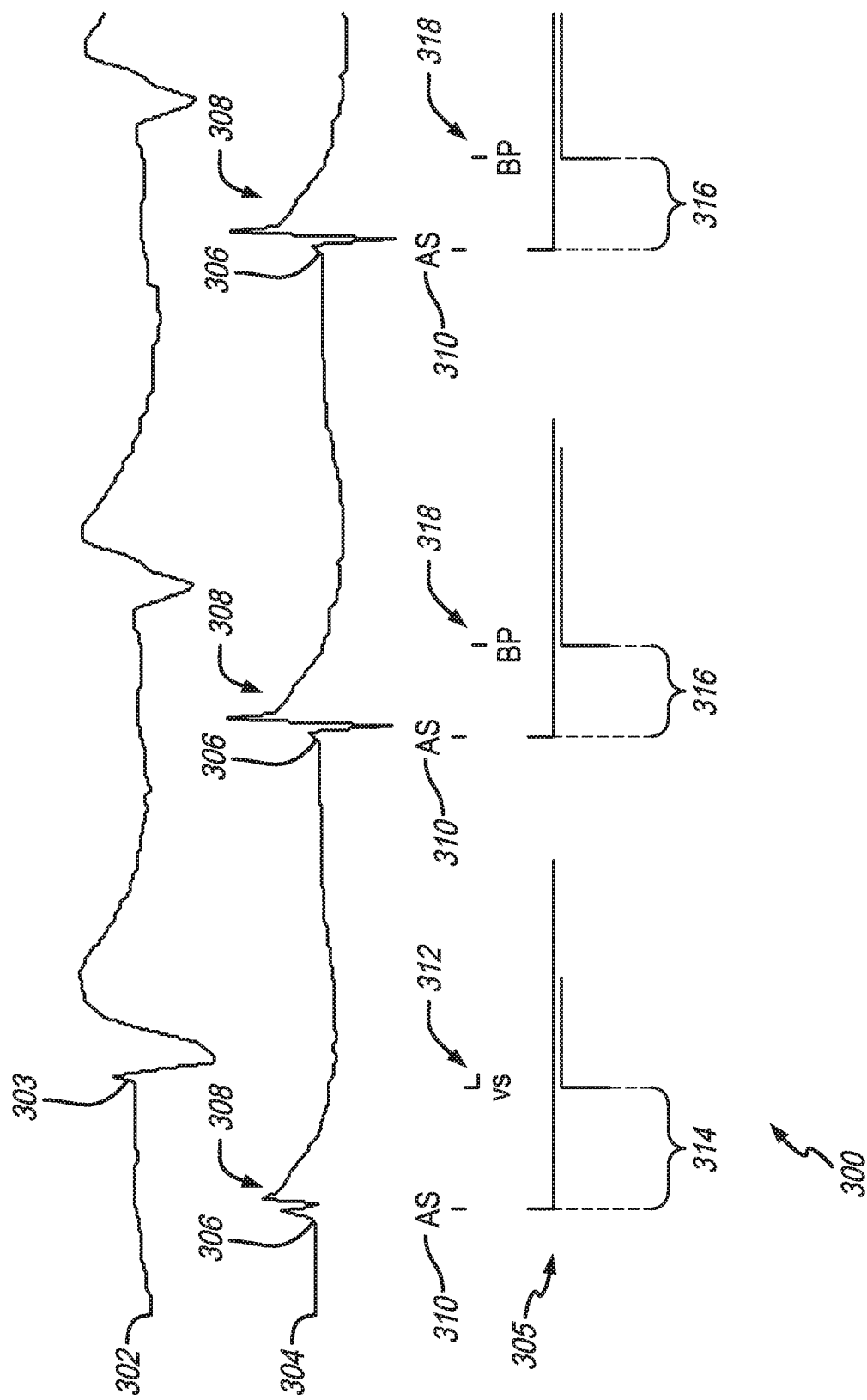
FIG. 3 illustrates electrocardiography and pacing delay data, according to an embodiment.

FIG. 3 illustrates electrocardiography and pacing delay data 300 in accordance with an embodiment. The illustrated electrocardiography data includes a heart electrocardiogram 302 and an atrial electrocardiogram 304. The heart electrocardiogram 302 and the atrial electrocardiogram 304 may have been acquired by the atrial sensing circuit 282 and/or the ventricular sensing circuits 284, shown in FIG. 2, of the IMD 100.

The atrial electrocardiogram 304 may be used by the negative hysteresis module 261 to identify intrinsic atrial conductions 308 of the heart 105. For example, the intrinsic atrial conductions 308 may include a series of peaks measured by the atrial sensing circuit 282. The negative hysteresis module 261 may identify a start 306 of the intrinsic atrial conduction 308 based on changes in slope of the atrial electrocardiogram 304. For example, when the negative hysteresis module 261 detects a change in the slope of the atrial electrocardiogram 304 above a predetermined threshold, the negative hysteresis module 261 may determine that the change of slope corresponds to a start 306 of the intrinsic atrial conduction 308 of the heart 105.

The heart electrocardiogram 302 may be used by the negative hysteresis module 261 to identify an intrinsic ventricular conduction 303 (e.g., ventricular sense) of the heart 105. Additionally or alternatively, the ventricular sense amplifier 284 may be used by the negative hysteresis module 261 to identify an intrinsic ventricular conduction 303 of the heart 105. The negative hysteresis module 261 may identify the intrinsic ventricular event conduction 303 based on changes in slope of the heart electrocardiogram 302. For example, when the negative hysteresis module 261 detects a change in the slope of the heart electrocardiogram 302 above a predetermined threshold, the negative hysteresis module 261 may determine that the change of slope corresponds to the intrinsic ventricular event conduction 303 of the heart 105.

Timing data of the intrinsic atrial events conductions 308 and the intrinsic ventricular conduction 303, for example determined by the negative hysteresis module 261, are illustrated in the pacing delay data 305. The start 306 of the intrinsic atrial conduction 308 may be represented by the AS indicator 310 (e.g., atrial sense). The intrinsic ventricular conduction 303 (also referred to as an intrinsic ventricular event) is represented by the VS indicator 312 (e.g., ventricular sense). The intrinsic AV conduction interval 314 represents an amount of time from the start 306 of the intrinsic atrial conduction 308 and the intrinsic ventricular conduction 303. For example, the intrinsic AV conduction interval 314 corresponds to a length of time the intrinsic ventricular conduction 303 occurs after the intrinsic atrial conduction 308. Based on the intrinsic AV conduction interval 314, the negative hysteresis module 261 may determine a paced AV delay 316.

The paced AV delay 316 determines when the IMD 100 delivers BiV fusion pacing, shown as BP 318 in FIG. 3, after or subsequent to the start 306 of the intrinsic atrial event conduction 308 (e.g., the AS indicator 310). For example, the paced AV delay 316 defines a period of time starting at the start 306 of the intrinsic atrial conduction 308 and ending at the BiV fusion paced event, BP 318. The paced AV delay 316 is calculated or defined by the negative hysteresis module 261 based on the intrinsic AV conduction interval 314 and a negative hysteresis delta. The negative hysteresis delta may be a programmable value that is programmable by a user (e.g. physician, clinician, etc.) and stored in the memory 294. In various embodiments, the negative hysteresis delta may be between ten and one hundred twenty milliseconds.

The negative hysteresis delta is configured to adjust a time at which the IMD 100 delivers the BiV fusion pacing in order to stimulate the LV 116 concurrently and/or simultaneously with the intrinsic conduction of the RV 114. For example, the negative hysteresis delta is used to define the paced AV delay 316 to be less than or shorter than the intrinsic AV conduction interval 314. The length of the paced AV delay 316 allows the BiV fusion pacing to support and/or occur with the intrinsic conduction of the heart 105. Defining the paced AV delay 316 to be less than the intrinsic AV conduction interval 314 increases a likelihood that the BiV fusion pacing delivered by the IMD 100 is not pre-empted by the intrinsic conduction of the heart 105.

In at least one embodiment, the negative hysteresis module 261 (or more generally, the controller 260) may calculate the paced AV delay based on Equation 1 shown below.

Paced AV delay=intrinsic AV conduction interval− Negative Hysteresis Delta       (Equation 1)

For example, the negative hysteresis module 261 may determine the intrinsic AV conduction interval 314 is 160 milliseconds. The negative hysteresis module 261 may subtract, from the intrinsic AV conduction interval 314, the negative hysteresis delta corresponding to, for example, 50 milliseconds as shown in Equation 1. Based on the AV conduction interval 314 and the negative hysteresis delta, the negative hysteresis module 261 may define the paced AV delay 316 to be 110 milliseconds. Additionally or alternatively, the negative hysteresis module 261 may continually monitor the heart electrocardiogram 302 after or subsequent to defining the paced AV delay 316. For example, the negative hysteresis module 261 may monitor the heart electrocardiogram 302 to determine if subsequent intrinsic ventricular conduction occurs prior to an end of (e.g., within, during) the paced AV delay 316 or pre-empts the BP 318. For example, the intrinsic ventricular conduction can change based on changes in the heart rate, changes in activity level of the patient, medication taken by the patient, and/or the like. When the intrinsic conduction of the heart 105 pre-empts the BiV pacing, the IMD 100 may not deliver BiV fusion pacing to the LV 116 and/or RV 114. Equation 1, which is used to specify a paced AV delay based on an intrinsic AV conduction interval and a Negative Hysteresis Delta, is an example of a Negative Hysteresis algorithm, or more specifically, an example of a Negative AV Hysteresis (NAHV) algorithm. In other words, any algorithm that is used to specify a paced AV delay based on an intrinsic AV conduction interval and a Negative Hysteresis Delta, can be referred to as Negative Hysteresis algorithm, or more specifically, as a Negative AV Hysteresis (NAHV) algorithm.

Additionally, the negative hysteresis module 261 may automatically adjust or redefine the paced AV delay 316 based on the detected subsequent intrinsic ventricular conduction. For example, the negative hysteresis module 261 (or more generally, the controller 260) may define an adjusted AV conduction interval based on the subsequent intrinsic ventricular conduction. Based on the adjusted AV conduction interval and the negative hysteresis delta, the negative hysteresis module 261 may define a new or second paced AV delay. The new paced AV delay determined by the negative hysteresis module 261 additionally adjusts the delivery of the BiV fusion pacing by the IMD 100. Thereby, the negative hysteresis module 261 (or more generally, the controller 260) provides adaptive BiV fusion pacing by adjusting the delivery of the BiV fusion pacing, BP 318, based on changes in the intrinsic conduction of the heart 105.

Optionally, the negative hysteresis module 261 (or more generally, the controller 260) may adjust or reassess the paced AV delay 316 at a measurement cycle. The measurement cycle represents a delay prior to the negative hysteresis module 261 measuring a new intrinsic AV conduction interval 314 to define a new paced AV delay. For example, the measurement cycle may occur after a predetermined number of cycles, which is stored in the memory 294. The predetermined number of cycles may correspond to a number of consecutively paced AV delays 316 or BiV fusion pacing pulses delivered by the IMD 100.

For example, the measurement cycle may occur on the 32nd cycle after or subsequent to the IMD 100 delivering 31 consecutive BiV fusion pacing pulses to the LV 116 and the RV 114. On the 32nd cycle, the measurement cycle, the negative hysteresis module 261 may measure the intrinsic conduction of the heart 105. For example, on the 32nd cycle, the IMD 100 may not deliver a BiV fusion pacing pulses. The negative hysteresis module 261 measures the intrinsic ventricular conduction (e.g., the intrinsic ventricular conduction 303) of the heart 105, and calculates a new intrinsic AV conduction interval (e.g., the intrinsic AV conduction interval 314). Based on the new intrinsic AV conduction interval and the negative hysteresis delta, the negative hysteresis module 261 calculates (e.g., utilizing Equation 1) a new or adjusted paced AV delay.

Additionally or alternatively, the negative hysteresis module 261 (or more generally, the controller 260) may reassess or adjust the paced AV delay based on more than one intrinsic AV conduction interval. The negative hysteresis module 261 may be configured to measure a plurality of intrinsic AV conduction intervals during a reassessment period. The reassessment period may correspond to a plurality of consecutive cycles (e.g., consecutive paced AV delays 316, consecutive BiV fusion pacing pulses). For example, the reassessment period may correspond to five cycles. It may be noted in other embodiments the reassessment period may include more than five cycles or less than five cycles. During the reassessment period, the paced AV delay can be set to a value that is greater than a baseline AV delay for one or more cardiac cycles, to thereby allow for intrinsic AV conduction, and thus, allow for an intrinsic AV conduction interval to be determined. In accordance with certain embodiments, the negative hysteresis module 261 can ensure that a delay between an atrial activation and an immediately following intrinsic ventricular depolarization does not exceed a specified maximum allowed AV delay by triggering ventricular pacing in response to the delay therebetween reaching the specified maximum allowed AV delay. Further, the negative hysteresis module 261 can ensure that none of the paced AV delays exceed a specified maximum allowed AV delay. For example, in accordance with an embodiment, the negative hysteresis module 261 can turn off a NAVH mode (discussed below) and return to delivering baseline BiV pacing in response to determining that at least one of a plurality of different paced AV delays, that are each determined based on the intrinsic AV conduction interval and one of the plurality of different negative hysteresis deltas, exceeds the specified maximum allowed AV delay. During the reassessment period, the IMD 100 may not deliver the BiV fusion pacing pulses, and the negative hysteresis module 261 may measure a series of intrinsic AV conduction intervals. The negative hysteresis module 261 may calculate an average or mean intrinsic AV conduction interval from the series of intrinsic AV conduction intervals acquired during the reassessment period. The mean intrinsic AV conduction may take into account recovery time and increase the accuracy of the overall intrinsic conduction time measurement by reducing the effect of outlying intrinsic AV conduction measurements. The negative hysteresis module 261 may calculate a new or adjusted paced AV delay based on the mean intrinsic AV conduction interval and the negative hysteresis delta. In other words, the intrinsic AV conduction interval (for use in Equation 1) can be specified to be equal to an average or mean of a plurality of measured intrinsic AV conduction intervals. Alternatively, the intrinsic AV conduction interval (for use in Equation 1) can be specified to be equal to an average or mean of just a few (e.g., the last three of five) intrinsic AV conduction intervals, or equal to the last of a plurality of intrinsic AV conduction intervals. Other variations are also possible.

Optionally, the new or adjusted paced AV delay defined subsequent to the measurement cycle may be continually adjusted or reassessed after a BiV pacing cycle. The BiV pacing cycle may include a predetermined number of cycles. The BiV pacing cycle may be a series of consecutive BiV fusion pacing pulses delivered by the IMD 100 prior to the negative hysteresis module 261 measuring a new intrinsic AV conduction interval 314. The predetermined number of cycles may be stored in the memory 294.

For example, the BiV pacing cycle may be 256 cycles corresponding to the IMD 100 delivering BiV fusion pacing 255 consecutive times to the LV 116 and the RV 114. On the 256th cycle, the negative hysteresis module 261 may measure the intrinsic conduction of the heart 105. For example, on the 256th cycle, the IMD 100 may not deliver BiV fusion pacing. The negative hysteresis module 261 measures an intrinsic ventricular conduction (e.g., the intrinsic ventricular conduction 303) of the heart 105, and calculates a new intrinsic AV conduction interval (e.g., the intrinsic AV conduction interval 314). Based on the new intrinsic AV conduction interval and the negative hysteresis delta, the negative hysteresis module 261 may calculate (e.g., utilizing Equation 1) a paced AV delay (e.g., the paced AV delay 316). In various embodiments, the negative hysteresis module 261 may continually transition from the measurement cycle and the BiV pacing cycle. By reassessing or adjusting the paced AV delay during the measurement cycle and the BiV pacing cycle, the negative hysteresis module 261 provides a rate-adaptive BiV fusion pacing in patients with intact AV conduction and LBBB.

Additionally or alternatively, the negative hysteresis module 261 may include an interventricular pacing delay between the LV 116 and the RV 114. The interventricular pacing delay (which can also be referred to as an LV-RV delay) may correspond to a difference in time between the BiV fusion paced delivered to the LV 116 and the BiV fusion pacing pulses delivered to the RV 114. Optionally, the negative hysteresis module 261 may keep track of the timing of refractory periods, blanking intervals, noise detection windows, evoked response detection windows, alert intervals, marker channel timing, and/or the like, which is known in the art. The NAVH mode is turned off, e.g., when baseline BiV pacing is being used, or when intrinsic AV conduction is allowed.

Whenever the negative hysteresis module 261 (and more generally, the controller 260) uses Equation 1 (or a similar equation) to calculate a paced AV delay (based on an intrinsic AV conduction interval and Negative Hysteresis Delta), the negative AV hysteresis (NAVH) mode can be said to be turned on. Whenever the negative hysteresis module 261 (and more generally, the controller 260) does not use Equation 1 (or a similar equation) to calculate a paced AV delay (based on an intrinsic AV conduction interval and Negative Hysteresis Delta), the negative AV hysteresis (NAVH) mode can be said to be turned off.

Returning to FIG. 2, the controller circuit 260 further includes an arrhythmia detector 262 for operating the IMD 100 as an implantable cardioverter/defibrillator device. The detector 262 determines desirable times to administer various therapies. For example, the detector 262 may detect the occurrence of an arrhythmia and automatically control the application of an appropriate electrical shock therapy to the heart aimed at terminating the detected arrhythmia. To this end, the controller circuit 260 further controls a shocking circuit 273 by way of a control signal 279. The shocking circuit 273 generates shocking pulses that are applied to the heart 105 of the patient through at least two shocking electrodes. The shocking pulses may be selected from the LA coil electrode 128, the RV coil electrode 136, and/or the SVC coil electrode 138 (all three electrodes shown in FIG. 1). The CAN 140 may act as an active electrode in combination with the RV coil electrode 136, or as part of a split electrical vector using the SVC coil electrode 138 or the LA coil electrode 128 (e.g., with the RV coil electrode 136 as a common electrode).

The controller circuit 260 may additionally include a morphology detector 264. The arrhythmia detector 262 and/or morphology detector 264 may be implemented in hardware as part of the controller circuit 260, or as software/firmware instructions programmed into the system 100 and executed on the controller circuit 260 during certain modes of operation.

The pulse generator 270, 272 deliver a pacing sequence (e.g., CRT pacing) from the LV electrode combination designated for the first LVEC pacing site. The pulse generator 270, 272 deliver a first LV pacing pulse in the pacing sequence from the LV electrode combination. As noted herein, the LV electrode combination includes an adjacent pair of LV electrodes. The pulse generator 270, 272 is coupled to the switch 274 that sets the adjacent pair of LV electrodes as cathodes when delivering the LV pacing pulse. Optionally, the pulse generator 270, 272 and switch 274, controlled by the site designation module 269 designate adjacent at least first and second LV electrodes as cathodes to simultaneously deliver at least a first pacing pulse.

Depending upon the implementation, the aforementioned components (e.g., the negative hysteresis module 261) of the controller circuit 260 may be implemented in hardware as part of the controller circuit 260, or as software/firmware instructions programmed into the device and executed on the controller circuit 260 during certain modes of operation. In addition, the modules may be separate software modules or combined to permit a single module to perform multiple functions. In addition, although shown as being components of the controller circuit 260, some or all of the components/modules described above may be implemented separately from the controller circuit 260 using application specific integrated circuits (ASICs) or the like.

The controller circuit 260 is further coupled to a memory 294 by a suitable data/address bus 296. The programmable operating parameters used by the controller circuit 260 are stored in the memory 294 and modified, as required, in order to customize the operation of IMD 100 to suit the needs of a particular patient. Such operating parameters define, for example, the amplitude or magnitude of the generated pacing pulses, wave shape, pulse duration, the measurement cycle, the BiV pacing cycle, and/or the like. Other pacing parameters may include base rate, rest rate, and/or circadian base rate. The memory 294 further may store one or more parameters that are used to define adjustments and/or of the CRT pacing, such as the intrinsic AV conduction interval 314, the paced AV delay 316, the start 306 of the intrinsic atrial conduction 308, the intrinsic ventricular conduction 303, and/or the like.

Optionally, the operating parameters of the implantable IMD 100 may be non-invasively programmed into the memory 294 through a radio frequency (RF) circuit 201 in communication with an external device such as an external programmer device 204 or a bedside monitor 202 (e.g., a programmer, trans-telephonic transceiver, or a diagnostic system analyzer, and/or the like). The RF circuit 201 may support a particular wireless communication protocol while communicating with the external programmer device 201 or the bedside monitor 202, such as Bluetooth low energy, Bluetooth, ZigBee, Medical Implant Communication Service (MICS), or the like. Protocol firmware corresponding to the wireless communication protocol may be stored in memory 194, which is accessed by the microcontroller 160. The protocol firmware provides the wireless protocol syntax for the controller circuit 260 to assemble data packets, establish communication links 203, and/or partition data received from the external programmer device 201 or the bedside monitor 202.

Optionally, the RF circuit 201 may support telemetry communication. For example, the RF circuit 201 may be activated by the controller circuit 260 through a control signal 206. The RF circuit 201 may allow IEGMs and status information relating to the operation of IMD 100 (contained in the controller circuit 260 or the memory 294) to be sent to the external device 202, and vice-versa, through the established communication link 203. An internal warning device 221 may be provided for generating perceptible warning signals to a patient and/or caregiver via vibration, voltage, or other methods.

The IMD 100 may further include an accelerometer or other physiologic sensor 208. Where a physiologic sensor 208 is used to adjust a pacing stimulation rate according to the exercise state (e.g., heart rate) of the patient, then the sensor may be referred to as a "rate-responsive" sensor. A physiological sensor 208 may alternatively or additionally be used to detect changes in cardiac output, changes in the physiological condition of the heart, and/or diurnal changes in activity (e.g., detecting sleep and wake states and arousal from sleep). Accordingly, the controller circuit 260 may respond to such changes by adjusting the various pacing parameters (such as rate, interatrial delay, interventricular pacing delay, AV delay, negative hysteresis delta, etc.) at which the pulse generators 270 and 272 generate stimulation pulses. While shown as being included within IMD 100, it is to be understood that the physiologic sensor 208 may also be external to the IMD 100. Optionally, the physiologic sensor 208 may still be implanted within or carried by the patient. A common type of rate responsive sensor 208 is an activity sensor incorporating an accelerometer or a piezoelectric crystal, which is mounted within the housing/case 140 of the IMD 100. Other types of physiologic sensors 208 are also known, such as sensors that sense the oxygen content of blood, respiration rate and/or minute ventilation, pH of blood, ventricular gradient, stroke volume, cardiac output, contractility, and the like.

The IMD 100 additionally includes a battery 210, which provides operating power to all of the circuits shown in FIG. 2. The makeup of the battery 210 may vary depending on the capabilities of IMD 100. If the system only provides low voltage therapy (e.g., for repetitive pacing pulses), a lithium iodine or lithium copper fluoride cell may be utilized. For a IMD that employs shocking therapy, the battery may be configured to be capable of operating at low current drains for long periods and then providing high-current pulses (for capacitor charging) when the patient requires a shock pulse. The battery 210 may also be configured to have a predictable discharge characteristic so that elective replacement time can be detected.

As further shown in FIG. 2, the IMD 100 has an impedance measuring circuit 212, which is enabled by the controller circuit 260 via a control signal 215. Uses for an impedance measuring circuit 212 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 212 is coupled to the switch 274 so that any desired electrode may be used.

The above described IMD 100 was described as an exemplary IMD. One of ordinary skill in the art would understand that one or more embodiments herein may be used with alternative types of implantable medical devices. Accordingly, embodiments should not be limited to using only the above described device 100.

Figure 4:
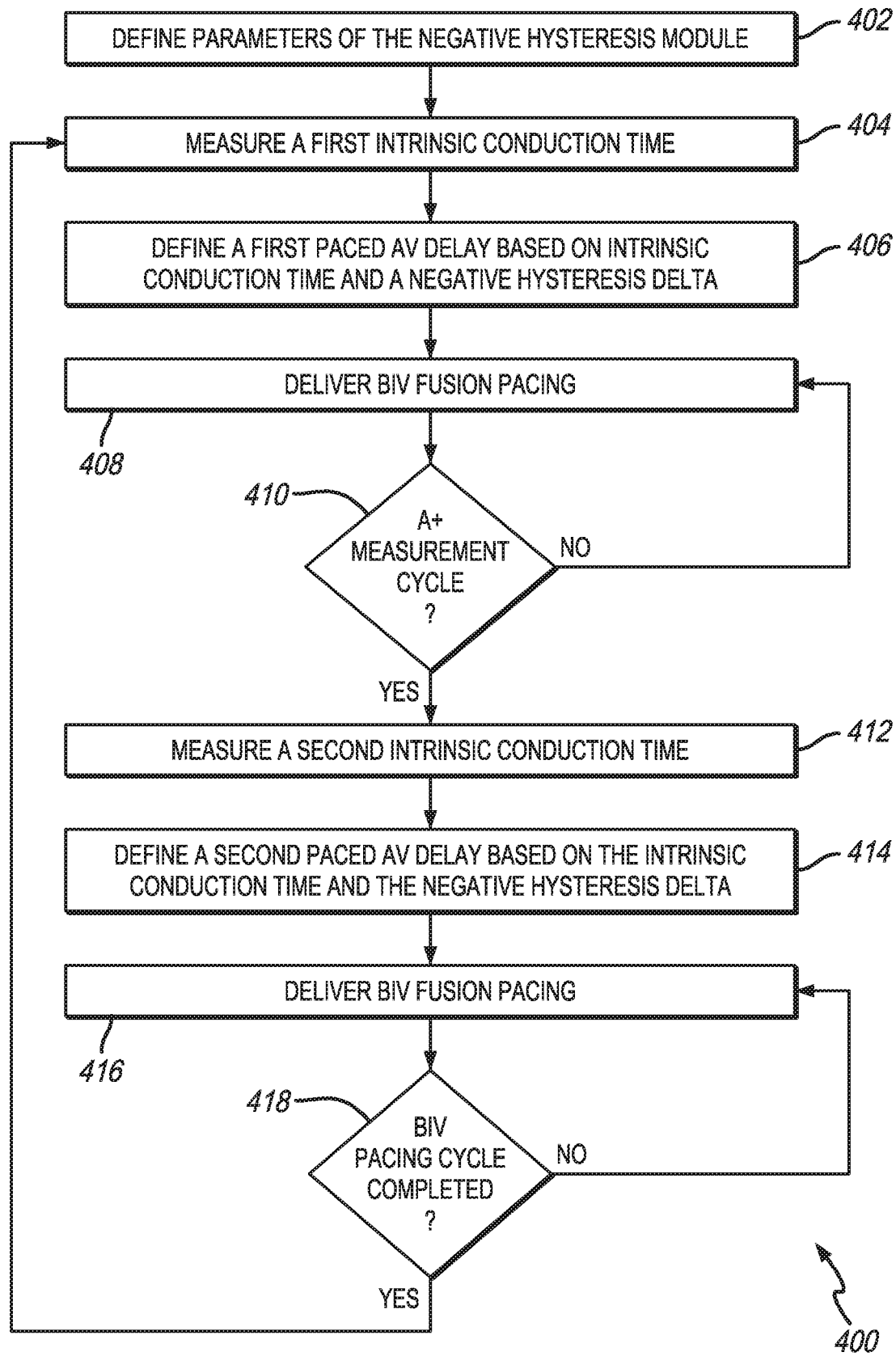
FIG. 4 illustrates a flow chart of a method for biventricular fusion pacing, according to an embodiment.

FIG. 4 illustrates a flowchart of a method 400 for rate adaptive BiV fusion pacing. The method 400 may be implemented as a software algorithm (e.g., the negative hysteresis module 261), package, or system that directs one or more hardware circuits or circuitry to perform the actions described herein. For example, the operations of the method 400 may represent actions to be performed by one or more circuits (e.g., the controller circuit 260) that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

Beginning at 402, the controller circuit 260 may define parameters of the negative hysteresis module 261. Optionally, the controller circuit 260 may define the parameters of the negative hysteresis module 251 based on instructions received from the external programmer 204 operated by a clinician (e.g., doctor, nurse). For example, a clinician may define or select the parameters to customize the BiV fusion pacing delivered by the IMD 100 via the communication link 203 based on the patient. In various embodiments, the clinician may define the parameters of the negative hysteresis module 261 during implantation and/or a medical examination of the IMD 100 based on echocardiography (ECHO) optimization, measurement of a QRS complex, and/or the like.

The parameters may include operational parameters of the negative hysteresis module 261 that are utilized by the negative hysteresis module 261 for the timing of the BiV fusion pacing. For example, the controller circuit 260 may define a default paced AV delay, one or more negative hysteresis deltas, a minimum AV delay (which can also be referred to as a minimum allowed AV delay), a maximum AV delay (which can also be referred to as a maximum allowed AV delay), an interventricular pacing delay (which can also be referred to as an RV-LV pacing delay), an intraventricular pacing delay (which can also be referred to as an LV1-LV2 pacing delay), a number of cycles for the measurement cycle, a number of cycles for a BiV pacing cycle, and/or the like. The default paced AV delay may be specified to be a length of time (e.g., 250 milliseconds) that is sufficiently long to allow for intrinsic AV conduction of the heart 105. More specifically, the default paced AV delay may be configured to delay the IMD 100 from delivering the BiV fusion pacing to allow the intrinsic ventricular conduction of the heart 105 to preempt the BiV fusion pacing.

The minimum AV delay may be a minimum length of time that the negative hysteresis module 261 may set the paced AV delay. For example, the minimum AV delay may be defined at 100 milliseconds, and a negative hysteresis delta may be defined at 50 milliseconds. Continuing with this example, the negative hysteresis module 261 may measure an intrinsic AV conduction interval of 140 milliseconds. As described in connection with Equation 1, the negative hysteresis module 261 may calculate a paced AV delay of 90 milliseconds by subtracting the negative hysteresis delta, of 50 milliseconds, from the intrinsic AV conduction interval, of 140 milliseconds. The negative hysteresis module 261 would compare the calculated paced AV delay with the minimum AV delay. If the calculated paced AV delay is less or shorter than the minimum AV delay, the negative hysteresis module 261 may set the paced AV delay as the minimum AV delay. By way of example, the minimum AV delay may range from 25 milliseconds to 120 milliseconds. The maximum AV delay may be a maximum length of time that the negative hysteresis module 261 may set the paced AV delay. Further, the IMD 100 can be configured to ensure that the maximum AV delay is not exceeded. For example, the controller 260 of the IMD 100 can ensure that a delay between an atrial activation and an immediately following ventricular activation does not exceed the specified maximum AV delay by triggering ventricular pacing in response to the delay therebetween reaching the specified maximum allowed AV delay.

The interventricular pacing delay may correspond to a difference in time between BiV fusion pacing delivered to the LV 116 and the BiV fusion pacing delivered to the RV 114. For example, the interventricular pacing delay may range from 5 milliseconds to 80 milliseconds. The interventricular pacing delay may be adjusted to customize the BiV fusion pacing pulses to the patient. For example, the interventricular pacing delay may be configured to occur subsequent to an intrinsic conduction of the RV 114.

At 404, the controller circuit 260 measures a first intrinsic conduction time. The first intrinsic conduction time may be a first intrinsic AV conduction interval 520 of the heart 105. For example, in connection with FIG. 5, the controller circuit 260 or the negative hysteresis module 261 may calculate an intrinsic AV conduction interval 520 based on measurements received by the atrial sensing circuit 282 and the ventricular sensing circuit 284 shown in FIG. 2.

Figure 5:
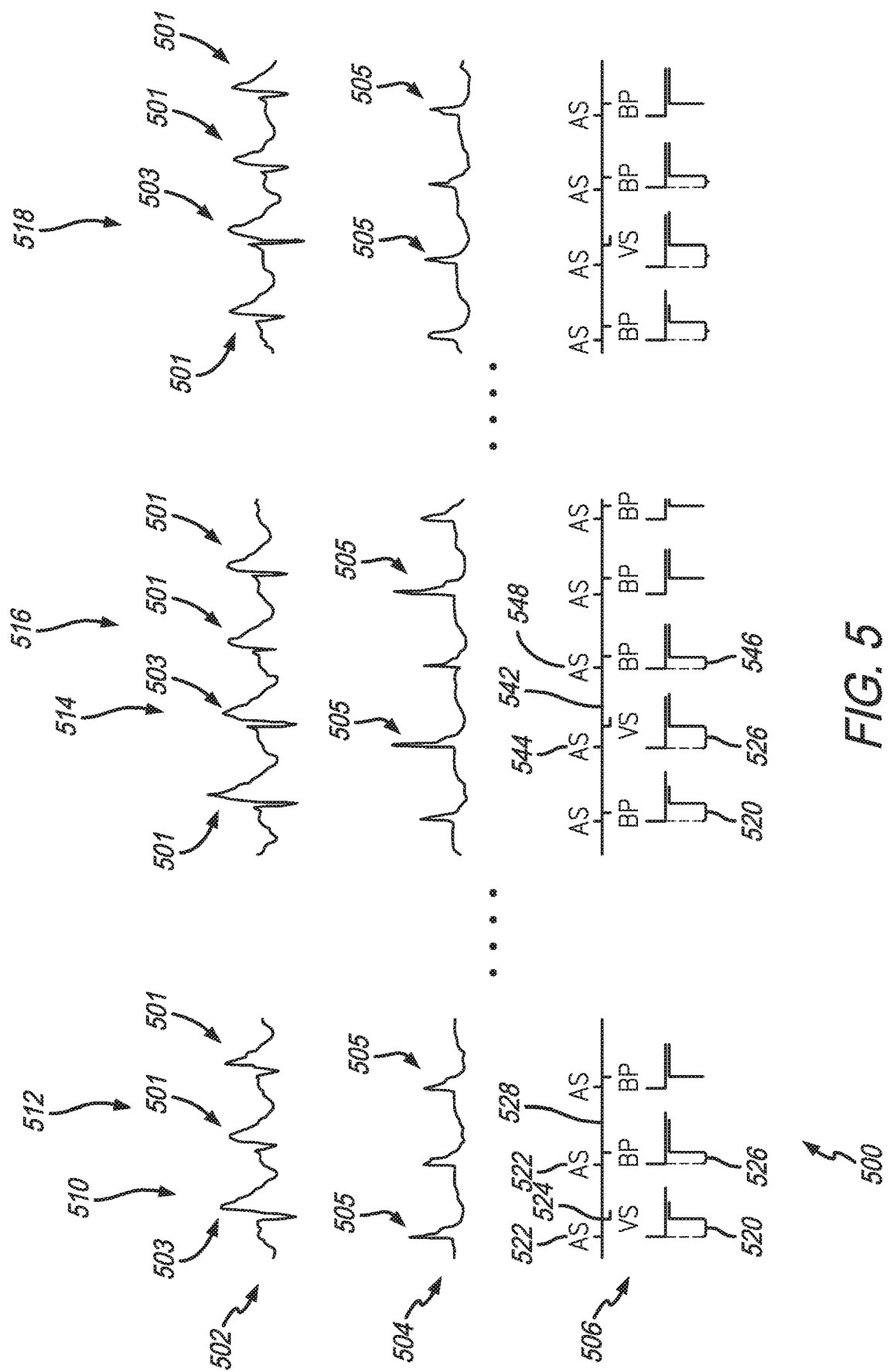
FIG. 5 illustrates electrocardiography and pacing delay data, according to an embodiment.

FIG. 5 illustrates electrocardiography and pacing delay data 500, in accordance with an embodiment. The data 500 may have been acquired by the IMD 100 during a series of cycles. The illustrated electrocardiography data includes a heart electrocardiogram 502 and an atrial electrocardiogram 504 acquired by the atrial sensing circuit 282 and/or the ventricular sensing circuit 284. The atrial electrocardiogram 504 illustrates a series of peaks 505, each corresponding to an intrinsic atrial conduction of the heart 105. A start of each peak 505 of the atrial electrocardiogram 504 may define a start of a cycle (e.g., 510, 512, 514, 516, 518) of the IMD 101. The heart electrocardiogram 502 includes peaks 503 that include intrinsic ventricular conduction, and peaks 501 in response to BiV fusion pacing.

Timing data of the intrinsic atrial conductions and the intrinsic ventricular conduction, for example determined by the negative hysteresis module 261, are illustrated in the pacing delay data 506. The intrinsic atrial depolarization is represented by the AS indicator 522. The intrinsic ventricular depolarization is represented by the VS indicator 524.

The negative hysteresis module 261 may measure the first intrinsic conduction time, such as the intrinsic AV conduction interval 520, during an initial cycle 510 of the IMD 100. During the initial cycle 510 the negative hysteresis module 261 may utilize the default paced AV delay defined at 402. The default paced AV delay may be configured to be longer than the intrinsic ventricular conduction time of the patient. For example, the intrinsic ventricular conduction of the patient occurs within or during the default paced AV delay. The negative hysteresis module 261 may measure a peak 503 that includes an intrinsic ventricular depolarization, which is represented by the indicator 524.

The negative hysteresis module 261 may calculate the first intrinsic AV conduction interval 520 based on when the intrinsic (or paced) atrial depolarization and the intrinsic ventricular depolarization occurs. The first intrinsic AV conduction interval 520 represents an amount of time from the intrinsic (or paced) atrial depolarization, occurring at the indicator 522, to the intrinsic ventricular depolarization occurring at the indicator 524. For example, the intrinsic AV conduction interval 520 corresponds to a length of time between the indicator 522 and the indicator 524.

At 406, the controller circuit 260 defines a first paced AV delay 526 based on the first intrinsic conduction time 520 and a negative hysteresis delta. The first paced AV delay 526 defines when the IMD 100 delivers BiV fusion pacing, represented by BP indicator 528, after or subsequent to the intrinsic atrial conduction (e.g., the AS indicator 522). The first paced AV delay 526 is calculated or defined by the negative hysteresis module 261 based on the first intrinsic AV conduction interval 520 and the negative hysteresis delta. As shown in Equation 1, the negative hysteresis module 261 may determine the first paced AV delay 526 by reducing or subtracting the intrinsic AV conduction interval 520 by the negative hysteresis delta. For example, the negative hysteresis module 261 may determine the intrinsic AV conduction interval 520 is 140 milliseconds. The negative hysteresis module 261 may subtract from the intrinsic AV conduction interval 520 the negative hysteresis delta corresponding to, for example, 50 milliseconds. Based on the AV conduction interval 520 and the negative hysteresis delta, the negative hysteresis module 261 may define the first paced AV delay 526 to be 90 milliseconds.

At 408, the IMD 100 delivers BiV fusion pacing to the heart 105. The BiV fusion pacing may include sequences of pacing pulses (e.g., one or more pacing pulses) generated by the pulse generators 270, 272 and routed by the switch 274 (shown in FIG. 2) to the LV 116 and the RV 114. For example, the controller circuit 260 detects a beginning of a cycle 512 at the intrinsic atrial conduction, shown as the AS indicator 522. After the first paced AV delay 526, corresponding to an end of the cycle 512, the controller circuit 260 may instruct the pulse generator 270 to generate a sequence of pulses for delivery to the RV lead 130, and instruct the pulse generator 272 to generate a sequence of pulses for delivery to the LV lead 124. The beginning of a cycle can alternatively be a paced atrial depolarization.

At 410, the controller circuit 260 determines whether the measurement cycle 514 is reached. The measurement cycle 514 may occur after a predetermined number of cycles subsequent or after the initial cycle 510. The controller circuit 260 may continually deliver the BiV fusion pacing to the heart 105, at 408, until the measurement cycle 514. For example, the controller circuit 260 may count a number of cycles after the initial cycle 510 until the measurement cycle 514 is reached, starting at the intrinsic atrial depolarization represented by an AS indicator 544.

When the measurement cycle is reached, at 412, the controller circuit 260 measures a second intrinsic conduction time. For example, the controller circuit 260 may adjust to the default paced AV delay to allow the intrinsic ventricular conduction, represented as a VS indicator 542, to pre-empt the BiV fusion pacing (e.g., the intrinsic ventricular conduction of the patient occurs within or during the default paced AV delay). The negative hysteresis module 261 may calculate the second intrinsic AV conduction interval 540 based on when the intrinsic atrial conduction, at the indicator 544, and the intrinsic ventricular conduction occurs at the indicator 542.

At 414, the controller circuit 260 adjusts the paced AV delay to correspond to a second paced AV delay 546 based on the intrinsic conduction time and the Negative Hysteresis delta. For example, the second paced AV delay 546 is calculated or defined by the negative hysteresis module 261 based on the second intrinsic AV conduction interval 540 and the negative hysteresis delta. As shown in Equation 1, the negative hysteresis module 261 may determine the second paced AV delay 546 by reducing or subtracting the second intrinsic AV conduction interval 540 by the negative hysteresis delta. For example, the negative hysteresis module 261 may adjust the paced AV delay to be the second intrinsic AV conduction interval 540 of 160 milliseconds, and subtract from the intrinsic AV conduction interval 520 the negative hysteresis delta of, for example, 50 milliseconds. Based on the second AV conduction interval 540 and the negative hysteresis delta, the negative hysteresis module 261 defines the second paced AV delay 546 to be 110 milliseconds.

At 416, the IMD 100 delivers BiV fusion pacing to the heart 105. For example, the controller circuit 260 detects a beginning of a cycle 516 at the intrinsic atrial conduction, shown as the AS indicator 548. After the second paced AV delay 546, corresponding to an end of the cycle 516, the controller circuit 260 may instruct the pulse generator 270 to generate a sequence of pulses for delivery to the RV lead 130, and the pulse generator 272 to generate a sequence of pulses for delivery to the LV lead 124.

At 418, the controller circuit 260 determines whether the BiV pacing cycle is completed. The BiV pacing cycle may include a predetermined number of cycles subsequent or after the measurement cycle 514. The controller circuit 260 may continually deliver the BiV fusion pacing to the heart 105, at 416, until a consecutive number of cycles of the BiV pacing cycle is reached. For example, the controller circuit 260 may count a number of cycles after the measurement cycle 514 until the predetermined number of cycles of the BiV pacing cycle is reached.

When the BiV pacing cycle is complete, the controller circuit 260 may continually repeat the method 400. For example, the controller circuit 260 may return to 404 to measure an intrinsic conduction time for a second initial cycle 518.

As described above, in accordance with certain embodiments of the present technology, the negative hysteresis module 261 may calculate the paced AV delay using Equation 1, which is: Paced AV delay=intrinsic AV conduction interval–Negative Hysteresis Delta. One potential problem with specifying a paced AV delay in this manner is that a patient may experience undesirably long AV delays if the patient develops AV block, which is a partial or complete interruption of impulse transmission from the atria to the ventricles. For example, assume that while a patient is not experiencing AV block their intrinsic AV conduction interval is 160 milliseconds, and the Negative Hysteresis Delta is specified to be 50 milliseconds. With this example, the paced AV delay would be 110 milliseconds (i.e., 160 milliseconds– 50 milliseconds=110 milliseconds). Now assume that at a later point in time the patient experiences AV block, which results in the negative hysteresis module 261 determining that the intrinsic AV conduction interval is 300 milliseconds (or timing out at 300 milliseconds). With this latter example, the paced AV delay would be 250 milliseconds (i.e., 300 milliseconds–50 milliseconds=250 milliseconds). Such a long paced AV delay can cause pacemaker syndrome, which may result in decreased cardiac output, loss of atrial contribution to ventricular filling, loss of total peripheral resistance response, and/or non-physiologic pressure waves, and more generally, may result in non-optimal hemodynamics which can cause fainting, dizziness, fatigue, shortness of breath and/or chest pain, any and all of which is/are undesirable. The aforementioned "timing out" can refer to the expiration of a timer that is used during a search for intrinsic AV conduction, wherein a ventricular backup pace is delivered if the timer reaches the point of "timing out."

A further potential problem with specifying a paced AV delay using Equation 1 is that device-sensed premature ventricular contractions (PVCs) may confuse or confound the device's measurement of a patient's intrinsic AV conduction interval (which measurement is used in Equation 1), resulting in inappropriately timed paced AV delays values, which would not result in fusion, and more generally, can compromise the efficacy of rate-adaptive BiV fusion pacing.

Another potential problem with specifying a paced AV delay using Equation 1 is that there may be certain periods of time when a patient would actually experience better hemodynamics using their intrinsic AV conduction rather than using rate adaptive BiV fusion pacing.

Further, it is also possible that during certain periods of time a patient would experience better hemodynamics using conventional non-rate adaptive BiV pacing, which will often be referred to hereafter as baseline BiV pacing, where a programmed non-adaptive baseline paced AV delay is used for non-fusion BiV pacing.

Certain embodiments of the present technology, which are described below, address at least some, and preferably all, of the above mentioned potential problems. More specifically, as will be described below, initially with reference to FIG. 6A, in accordance with certain embodiments of the present technology, one or more measures of efficacy are determined from time-to-time (e.g., periodically, or aperiodically in response to a triggering event) for different types of BiV pacing, for different paced AV delays, as well as for when intrinsic AV conduction is allowed, in order to determine and utilize (or allow) the type of BiV pacing or intrinsic AV conduction that during different periods of time results in the best relative efficacy. Such embodiments may be beneficial, for example, when used with patients that intermittently experience AV block.

Figure 6A:
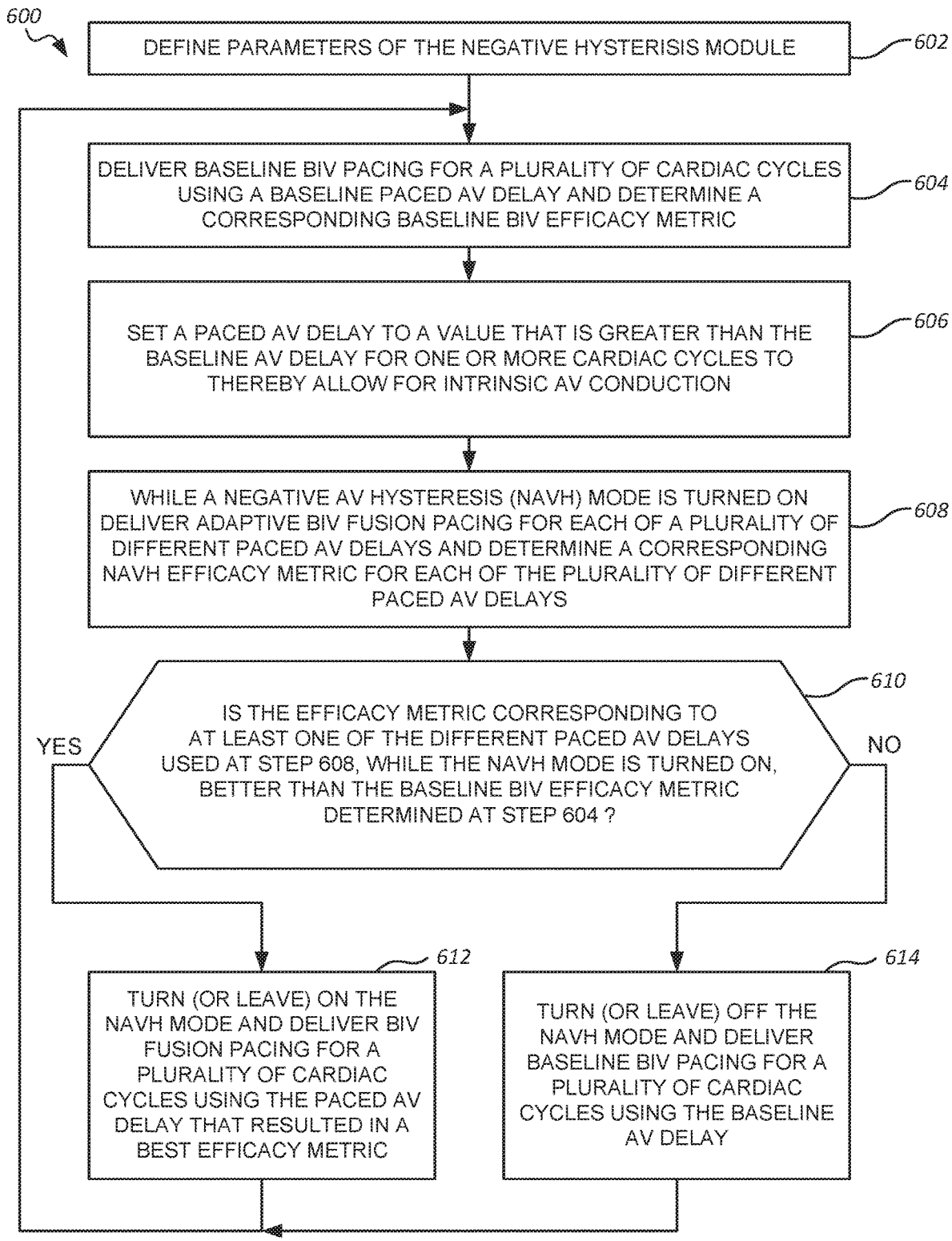
FIGS. 6A and 6B illustrate flow charts of methods for biventricular pacing, according to further embodiments.

The flowchart of FIG. 6A will now be used to describe a method 600 for delivering BiV pacing in accordance with certain embodiments of the present technology. The method 600 may be implemented as a software algorithm (e.g., the negative hysteresis module 261), package, or system that directs one or more hardware circuits or circuitry to perform the actions described herein. For example, the operations of the method 600 may represent actions to be performed by one or more circuits (e.g., the controller circuit 260) that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

Beginning at 602, the controller circuit 260 may define parameters of the negative hysteresis module 261, in the same or a similar manner as discussed above with reference to step 402 in FIG. 4. Optionally, the controller circuit 260 may define the parameters of the negative hysteresis module 251 based on instructions received from the external programmer 204 operated by a clinician (e.g., doctor, nurse). For example, a clinician may define or select the parameters to customize the BiV fusion pacing delivered by the IMD 100 via the communication link 203 based on the patient. In various embodiments, the clinician may define the parameters of the negative hysteresis module 261 during implantation and/or a medical examination of the IMD 100 based on echocardiography (ECHO) optimization, measurement of a QRS complex, and/or the like.

The parameters may include operational parameters of the negative hysteresis module 261 that are utilized by the negative hysteresis module 261 for the timing of the BiV fusion pacing. For example, the controller circuit 260 may define a default paced AV delay, one or more negative hysteresis deltas, a minimum AV delay, an interventricular pacing delay, a number of cycles for the measurement cycle, a number of cycles for a BiV pacing cycle, and/or the like. Exemplary details of many of these parameters were already described above with reference to step 402 in FIG. 4, and thus, need not be repeated here. Further parameters that may be defined at step 602 include, but are not limited to, a baseline paced AV delay, exemplary details of which are described below.

Still referring to FIG. 6A, at 604, the IMD 100 delivers baseline BiV pacing for a plurality of cardiac cycles (e.g., 5 cycles, but not limited thereto) using a baseline paced AV delay, and the controller circuitry 260 determines a corresponding baseline BiV efficacy score. The baseline paced AV delay may be a length of time that is selected to closely reflect typical non-fusion BiV paced programming, which is intended to be utilized in the absence of intrinsic AV conduction (e.g., if AV block were to develop). For example, the baseline paced AV delay may be within the range from 100 milliseconds to 150 milliseconds, inclusive, but is not limited thereto. The baseline paced AV delay is different than (and will likely be significantly shorter than) the default paced AV delay, which was discussed above. Exemplary efficacy scores, which are discussed below, can include, but are not limited to, measures of pulmonary artery pressure (PAP) and/or measures of QRS complex morphology.

Still referring to FIG. 6A, at 606, a paced AV delay is set to a value that is greater than the baseline AV delay for one or more cardiac cycles (e.g., five cycles, but not limited thereto), to thereby allow for intrinsic AV conduction, and an intrinsic AV conduction interval is determined by the controller circuit 260. Step 606 can involve extending the baseline AV delay by an amount (e.g., 100 milliseconds) that is sufficient to allow for intrinsic AV conduction. Alternatively, step 606 can involve setting the paced AV delay to the default paced AV delay explained above. The intrinsic AV conduction interval determined at step 606 can be an average or mean of all (e.g., five) of the AV intervals where there is intrinsic AV conduction, an average or mean of just the last few (e.g., the last three of five) AV intervals where there is intrinsic AV conduction, or simply defined to be equal to the last (e.g., the fifth of five) AV interval where there is intrinsic AV conduction. Other variations are also possible and within the scope of this embodiment. As will be described in additional detail below, with reference to step 606' in FIG. 6B, in accordance with certain embodiments an intrinsic AV conduction efficacy score may be determined.

Still referring to FIG. 6A, at 608, the negative AV hysteresis (NAVH) mode is turned on, and while the NAVH is turned on, adaptive BiV fusion pacing is delivered for each of a plurality of different paced AV delays, and a corresponding NAVH efficacy score is determined for each of the plurality of paced AV delays. In accordance with specific embodiments, each of the plurality of different paced AV delays is determined based on the intrinsic AV conduction interval determined at step 606 and a different negative hysteresis delta. For example, there can be five (or some other number of) different negative hysteresis deltas, in which case five (or some other number of) different paced AV delays may be tested at step 608, with each being tested for a plurality of cardiac cycles (e.g., five cycles, but not limited thereto). The plurality of different negative hysteresis deltas, which may be defined at step 602, can be, for example, 10 milliseconds, 20 milliseconds, 30 milliseconds, 40 milliseconds and 50 milliseconds, but are not limited thereto. Assuming that the intrinsic AV conduction detected at step 606 is 180 milliseconds, and that Equation 1 discussed above is used to determine the different paced AV delays, then the different paced AV delays that are tested at step 608 would be 170 milliseconds, 160 milliseconds, 150 milliseconds, 140 milliseconds and 130 milliseconds. In accordance with certain embodiments, at least one of the pulses delivered during each cycle of the adaptive BiV fusion pacing at step 608 is timed to be delivered concurrently with an intrinsic right ventricular conduction to thereby achieve fusion. Continuing with this example, a separate corresponding NAVH efficacy score would be determined for each of the aforementioned paced AV delays. Exemplary efficacy scores are described below.

Various different efficacy scores were described above as being determined as parts of steps 604, 606 (or 606') and 608. More specifically, at step 604 a baseline efficacy score is determined; at step 606 (or 606') an intrinsic AV conduction efficacy score may be determined; and at step 608 a separate corresponding NAVH efficacy score is determined for each of the plurality of different paced AV delays that are tested. Preferably, the way each of these various types of efficacy scores are determined is the same, so that they can be compared to one another for the purpose of determining which type of pacing, during any period of time, is preferred, which may change over time. Exemplary ways of determining such efficacy scores will now be described below. However, it should be noted that these are examples that are not intended to be all encompassing, as will be appreciated by one of ordinary skill in the art.

In accordance with certain embodiments, each efficacy score is a QRS score that can be based on QRS width, overall QRS morphology, and/or the like. In general, the narrower QRS width the better the efficacy, and the wider QRS width the worse the efficacy. This is because a wide QRS complex (e.g., exceeding 100 milliseconds) is often associated with bundle branch block and/or some other ventricular activation abnormality. Accordingly, where a QRS score (and more generally, an efficacy score) is based on QRS width, the narrower the QRS width that occurs in response to a specific type of pacing, the higher the efficacy score, assuming the higher the score the better. Where a QRS score (and more generally, an efficacy score) is based on QRS morphology, the morphology of one or more QRS complexes can be compared to a predefined and stored optimal or preferred QRS complex template, with the greater the similarity the higher the score. It would also be possible to combine multiple measures of efficacy into a single efficacy score. Depending on the metric, and more generally, depending upon implementation, the "best" metric may be the one with the lowest value, or the one with the highest value. For example, where an efficacy score is the QRS width, or proportional thereto, then the best efficacy score would be the one with the lowest value. For another example, where the efficacy score is a measure of similarity to an optimal or preferred QRS morphology template, then the best efficacy score would be the one with the highest value. Alternatively, or additionally, efficacy scores can be based on one or more hemodynamic measurements obtained using one or more sensors, such as, but not limited to, an implantable sensor that measures pulmonary arterial pressure (PAP) or a surrogate thereof. Depending upon implementation, each such value can be converted to a score, which may be directly of inversely proportional to the value.

As noted above, efficacy scores can be based, inter alia, on one or more hemodynamic measurements obtained using one or more sensors, such as, but not limited to, an implantable sensor that measures pulmonary arterial pressure (PAP). Exemplary sensors that can be implanted in a pulmonary artery to obtain measures of PAP are described in U.S. Pat. No. 8,353,841, entitled "Apparatus and Method for Sensor Deployment and Fixation," which is incorporated herein by reference. An exemplary implantable sensor that provides for ambulatory measurements of PAP is marketed is part of The CardioMEMS™ HF System, which uses a small pressure sensor implanted in a distal pulmonary artery via a safe right heart catheterization procedure. This small pressure sensor includes an inductor coil and a pressure-sensitive capacitor that create a resonant circuit at a specific frequency that is effected by blood pressure, and thus, changes as blood pressure changes, and is thereby useful to measure PAP. The CardioMEMS™ HF System is available from St. Jude Medical Inc. (headquartered in St. Paul, Minn.). The measurements of PAP obtained using an implanted sensor can be transmitted wirelessly directly from the implanted sensor to the IMD 100, or alternatively, from the implanted sensor to an external device (e.g., 700), and then from the external device to the IMD 100. Other variations are also possible.

In accordance with certain embodiments, the optimal or preferred QRS morphology template, which is compared to sensed QRS complexes to obtain efficacy scores, can be determined as follows. Initially, for each of a plurality of different sets of BiV pacing parameters, a sensor implanted in the pulmonary artery is used to obtain a corresponding measure of PAP, and one or more implanted electrodes is/are used to detect a QRS complex corresponding to each measure of PAP. Exemplary details of such a sensor were described above. Such embodiments can further include identifying which of the measures of PAP is a best one of the measures of PAP, and saving, as a QRS complex template, the detected QRS complex that corresponds to the best one of the measures of PAP. The best measure of PAP can be, e.g., the lowest PAP. Thereafter, when efficacy scores are determined, e.g., as part of steps 606, 606' and/or 608, detected QRS complexes are compared to the saved QRS complex template that corresponds to the best one of the measures of PAP to determine a similarity thereto.

Referring again to FIG. 6A, at 610 there is a determination of whether the efficacy score corresponding to at least one of the plurality of different paced AV delays used at step 608, while the NAVH mode is turned on, is better than the baseline BiV efficacy score determined at step 604. If the efficacy score corresponding to at least one of the plurality of different paced AV delays used at step 608, while the NAVH mode is turned on, is better than the baseline BiV efficacy score determined at step 604 (i.e., if the answer to the determination at step 610 is YES), then at step 612 the NAVH mode is turned (or left) on and BiV fusion pacing is delivered at step 612 for a plurality of cardiac cycles using the paced AV delay that resulted in a best one of the efficacy scores. If the efficacy score corresponding to at least one of the plurality of different paced AV delays used at step 608, while the NAVH mode is turned on, is not better than the baseline BiV efficacy score determined at step 604 (i.e., if the answer to the determination at step 610 is NO), then at step 614 the NAVH mode is turned (or left) off and baseline BiV pacing is delivered for a plurality of (e.g., 256) cardiac cycles using the baseline AV delay. The plurality of cardiac cycles referred to in steps 612 and 614 in FIG. 6A can be specified to be a specific number of cycles, such as 256 cardiac cycles, or alternatively can be specified as a period of time, e.g., four minutes. After pacing is performed at one of steps 612 and 614 for the specified number of cycles or the specified period of time, then flow returns to step 604, as shown in FIG. 6A. More generally, steps 604-614, or portions thereof, can be repeated from time-to-time.

In accordance with certain embodiments, the method 600 can also include monitoring an activity level and/or posture of the patient, and returning to step 604 (and thereby repeating at least some of steps 604-614) each time the activity level of the patient changes beyond a threshold, changes from one type of activity level to another type of activity level, or changes from one posture to another. In one such an embodiment, the type of BiV pacing selected at steps 610-614 can be continued until there the activity level of the patient changes beyond a threshold, changes from one type of activity level to another type of activity level, or changes from one posture to another. The patient's activity level can be monitored based on heart rate (HR), or using an activity sensor (e.g., a 3D accelerometer), or a combination thereof, but is not limited thereto. The patient's posture can be determined, e.g., using a 3D accelerometer or some other type of posture sensor. Such sensor can be types of physiologic sensor(s) 208 described above with reference to FIG. 2.

Figure 6B:
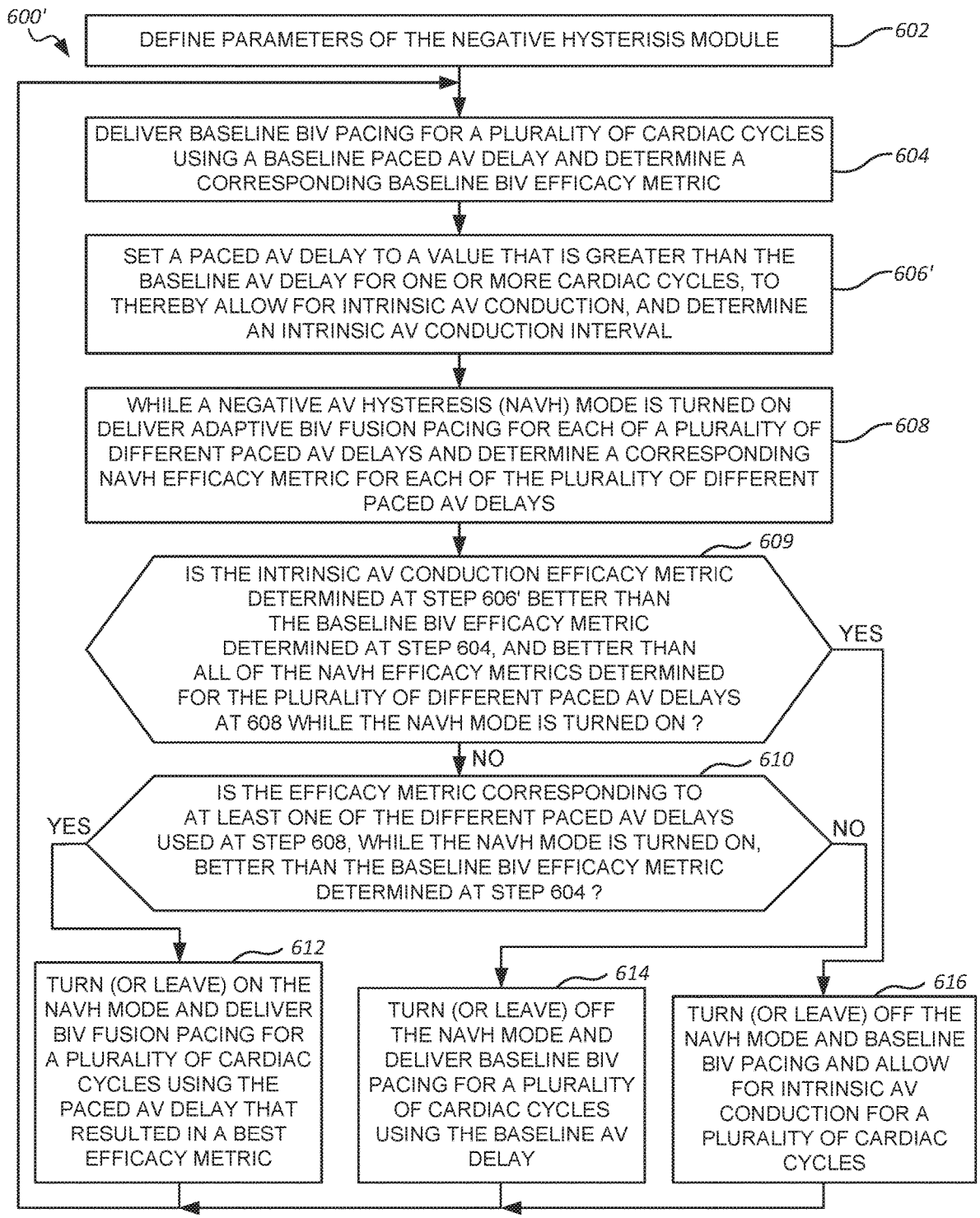

The flowchart of FIG. 6B will now be used to describe a method 600' for delivering BiV pacing in accordance with alternative embodiments of the present technology. The steps in FIG. 6B that are the same as those in FIG. 6A, are labeled the same, and the explanations thereof need not be repeated. Referring to FIG. 6, a difference between step 606 described above with reference to FIG. 6A and step 606' shown in FIG. 6B is that in FIG. 6B, step 606' also includes determining a corresponding intrinsic AV conduction efficacy score, which is indicative of efficacy that occurs when intrinsic AV conduction occurs. Exemplary efficacy scores were discussed above.

Still referring to FIG. 6B, an additional step in FIG. 6B compared to FIG. 6A, is step 609. At 609 there is a determination of whether the intrinsic AV conduction efficacy score determined at step 606' is better than the baseline BiV efficacy score determined at step 604, and better than all of the NAVH efficacy scores determined for the plurality of different paced AV delays at step 608 while the NAVH mode is turned on. If the intrinsic AV conduction efficacy score (determined at step 606') is better than the baseline BiV efficacy score (determined at step 604), and better than all of the NAVH efficacy scores determined for the plurality of different paced AV delays (at step 608) while the NAVH mode is turned on (i.e., if the answer to the determination at step 609 is YES), then the NAVH mode is turned (or left) off, and the baseline BiV pacing is turned (or left) off, and intrinsic AV conduction is allowed for a plurality of cardiac cycles (e.g., for 256 cycles), as indicated at step 616. If the answer to the determination at step 609 is NO, then flow goes to step 610, which was already explained above with reference to FIG. 6A.

The plurality of cardiac cycles referred to in steps 612, 614 and 616 in FIG. 6B can be specified to be a specific number of cycles, such as 256 cardiac cycles, or alternatively can be specified as a period of time, e.g., four minutes. After pacing is performed at one of steps 612 and 614, or intrinsic AV conduction is allowed at step 616, for the specified number of cycles or the specified period of time, then flow returns to step 604, as shown in FIG. 6B. More generally, steps 604-616, or portions thereof, can be repeated from time-to-time.

In accordance with certain embodiments, the method 600' can also include monitoring an activity level of the patient, and returning to step 604 (and thereby repeating at least some of steps 604-616) each time the activity level of the patient changes beyond a threshold, or changes from one type of activity level to another type of activity level. In one such an embodiment, the type of BiV pacing selected at steps 609-616 can be continued until there the activity level of the patient changes beyond a threshold, or changes from one type of activity level to another type of activity level, such as from resting to active, or vice versa, but not limited thereto. The patient's activity level can be monitored based on heart rate (HR), or using an activity sensor (e.g., a 3D accelerometer), or a combination thereof, but is not limited thereto. Alternatively, or additionally, the method 600' can also include monitoring a posture of the patient, and returning to step 604 (and thereby repeating at least some of steps 604-616) each time the patient's posture changes, e.g., from supine to erect, or vice versa. Such an activity sensor or posture sensor can be one of the physiologic sensor(s) 208 described above with reference to FIG. 2.

A PVC is ventricular contraction not initiated by the atrium, i.e., not resulting from normal propagation of an action potential that propagates from the atrium through the atrioventricular node (AV node) and the atrioventricular bundle (AV bundle or His bundle) to the ventricles. As noted above, a potential problem with specifying a paced AV delay using Equation 1 is that device-sensed PVCs may confuse or confound the device's measurement of a patient's intrinsic AV conduction interval (which measurement is used in Equation 1). This can undesirably result in inappropriately timed paced AV delays values, which would not result in fusion, and more generally, can compromise the efficacy of rate-adaptive BiV fusion pacing. For example, a PVC may cause the IMD 100 to determine that a patient's intrinsic AV conduction interval is significantly shorter than it actually is, which can result in one or more paced AV delays determined using Equation 1 and used when the NAVH mode is turned on being much shorter than they actually should be. Certain embodiments of the present technology monitor for one or more PVCs and account for PVC(s) if/when detected.

There are various ways that a PVC can be detected that includes monitoring of the ventricular channel. In accordance with certain embodiments, a PVC is detected if two consecutive ventricular events are detected in the ventricular channel without an intervening atrial event being detected in the atrial channel. Here, the second of the two consecutive ventricular events detected without an intervening atrial event is the PVC. Additionally, or alternatively, a PVC can be detected if a ventricular event is detected in the ventricular channel, but an atrial event is not detected in the atrial channel within a specified time period preceding (e.g., between about 400 and 600 milliseconds) the ventricular event. For another example, since the morphology of a PVC is different than the morphology of a ventricular contraction initiated by the atrium, a morphology analysis can be performed to detect a PVC. Such a morphology analysis can include, for example, determining and storing an intrinsic QRS complex template, determining a similarity between sensed QRS complexes and the stored template, and classifying a sensed QRS complex as a PVC if the similarity is below a specified threshold. The stored intrinsic QRS complex template can be static, or more preferably, can be updated from time-to-time (e.g., whenever an intrinsic AV conduction interval is re-determined as part of step 606 or 606'). In other words, step 606 or 606' can include detecting and storing an intrinsic QRS complex template. Alternative techniques for detected PVCs are also possible, and can be used with embodiments of the present technology.

In accordance with certain embodiments, step 604 (from FIG. 6A or 6B) can include determining whether one or more PVCs occurred while delivering the baseline BiV pacing, and in response to determining that at least one PVC occurred while delivering the baseline BiV pacing, the corresponding baseline BiV efficacy score can be determined in a manner that is unaffected by any PVC(s). Similarly, step 606 or 606' (from FIG. 6A or 6B) can include determining whether at least one PVC occurred while the AV delay is extended by the amount sufficient to allow for intrinsic AV conduction, and in response to determining that at least one PVC occurred while the AV delay is extended by the amount sufficient to allow for intrinsic AV conduction, the intrinsic AV conduction interval can be determined in a manner that is unaffected by any PVC(s). Similarly, step 608 (from FIG. 6A or 6B) can include determining whether at least one PVC occurred while delivering the adaptive BiV fusion pacing, and in response to determining that at least one PVC occurred while delivering the adaptive baseline BiV pacing, the corresponding NAVH efficacy score(s) can be determined in a manner that is unaffected by any PVC(s). One way to determine an efficacy score in a manner that is unaffected by any PVC(s) is to ignore, exclude or otherwise not use a measurement (used to determine an efficacy score) that is associated with a cardiac cycle in which a PVC was detected. Other variations are possible, and within the scope of embodiments described herein.

Referring back to FIGS. 6A and 6B, instances of step 608 are performed by the IMD 100 to attempt to optimize the paced AV delay that is used during adaptive BiV fusion pacing. In accordance with certain embodiments, the IMD 100 can also attempt to optimize an inter-ventricular (LV-RV) delay, which is the delay between delivery of a stimulation pulse to the left ventricle and delivery of a stimulation pulse to the right ventricle. This can involve, for example, after selecting a preferred paced AV delay (from a plurality of paced AV delays that are tested at step 608), for each of a plurality of different inter-ventricular (LV-RV) delays, delivering BiV pacing (using the preferred paced AV delay) for a plurality of cardiac cycles and determining a corresponding LV-RV efficacy score. Such embodiments can also include the controller 260 selecting, for use during further BiV pacing, the one of the LV-RV delays corresponding to a best LV-RV efficacy score. Exemplary efficacy scores that can be determined and compared to one another were already described above, and thus, need not be repeated.

As explained above, the IMD 100 may be configured for single site or multi-site left ventricular (MSLV) pacing. In multi-site left ventricular (MSLV) pacing, which can also be referred to as multipoint left ventricular pacing (MPP), pacing pulses are delivered at more than one site within the LV chamber during each pacing cycle. The multi-pole LV lead 124, described above with reference to FIG. 1, is an example of a lead that can be used to perform MPP pacing. Exemplary MPP pacing vectors were also described above with reference to FIG. 1. MPP pacing has been shown to significantly increase responder rates, as indicated by a greater than 15% decrease in end systolic volume (ESV), as well as improving ejection fraction (EF) and New York Heart Association (NYHA) functional classification in both ischemic and non-ischemic patients. Utilization of MPP can also improve acute hemodynamic response (LV dP/dt), result in QRS narrowing, decrease left ventricular total activation time, and/or increase the percentage of ventricular mass captured during LV pacing, all of which are desirable. In addition, prior work has shown that targeted biventricular pacing of sites of latest LV electrical activation (QLV) has been shown to increase LV dP/dt, and narrow the QRS as well. Further, similar results on LV dP/dt and QRS narrowing have been observed with biventricular fusion pacing strategies.

In accordance with certain embodiments, the IMD 100 can also attempt to select a preferred (and preferably optimal) MPP pacing vector and/or optimize an intra-ventricular (LV1-LV2) delay, which is the delay between delivery of stimulation pulses to two distinct locations in the left ventricle. The range of possible LV1-LV2 delays can be, e.g., between 5 to 80 milliseconds, but is not limited thereto. As noted above, exemplary MPP pacing vectors were also described above with reference to FIG. 1. Various different MPP pacing vectors can be tested to determine which vector is preferred, or potentially, to determine if single site LV pacing provides for a better efficacy than MPP pacing. When the IMD 100 delivers single site LV pacing, it can be said that the MPP mode is turned off, and then the IMD 100 delivers MPP pacing, it can be said that the MPP mode is turned on.

In accordance with certain embodiments, while the NAVH mode is turned on, the IMD 100 can make repetitive assessments of AV intrinsic conduction time (e.g., every 256 cycles) to account for changes in patient's heart rate, AV condition, and activity level. Further, with the MPP mode turned on, the MPP 100 can then (e.g., after an initially fused LV1 pacing pulse) apply a second timed LV2 pacing stimuli from a different vector, thus combining the capabilities of Negative Hysteresis fusion pacing with that of a multipoint LV pacing capability. The two LV pacing sites, selected for use in MPP pacing, can be selected, e.g., to achieve a latest LV electrical (QLV) activation and/or a largest anatomic separation (increased LV stimulation area), which may provide for an additional incremental benefit. After the multiple LV locations for use in MPP pacing are selected, then for each of a plurality of different intra-ventricular (LV1-LV2) delays, BiV pacing (that includes pacing at multiple LV locations) is delivered for a plurality of cardiac cycles (e.g., 5 cycles) and a corresponding LV1-LV2 efficacy score can be determined. Exemplary LV1-LV2 delays, that may be tested, can include 5, 10 milliseconds, 20 milliseconds, 30 milliseconds and 40 milliseconds, but are not limited thereto, wherein each LV1-LV2 delay indicates a delay between pacing at the LV1 location and the LV2 location. For example, an LV1-LV2 delay of 20 milliseconds, would mean that the LV2 location is paced 20 milliseconds after the LV1 location. It is also possible that LV1-LV2 delays may be negative values, which would indicate that the LV2 location is paced before the LV1 location. For example, an LV1-LV2 delay of −20 milliseconds, would mean that the LV2 location is paced 20 milliseconds prior to the LV1 location. Exemplary efficacy scores were already described above, and thus, need not be described again.

Referring again to FIGS. 6A and 6B, in accordance with certain embodiments, when performing step 604, the IMD 100 (and more specifically, the controller 260 thereof) can ensure that a delay between an atrial activation and an immediately following ventricular activation does not exceed a specified maximum allowed AV delay by triggering ventricular pacing in response to the delay therebetween reaching the specified maximum allowed AV delay. The maximum allowed AV delay (which can also be referred to more succinctly as the maximum AV delay) can be defined during step 602, as mentioned above. An exemplary value for the maximum allowed AV delay can be 250 milliseconds, but is not limited thereto. Similarly, when performing other steps, such as step 606, 606' and/or 608, the IMD 100 (and more specifically, the controller 260 thereof) can ensure that a delay between an atrial activation and an immediately following ventricular activation does not exceed the specified maximum allowed AV delay. In accordance with certain embodiments, ensuring that none of the paced AV delays exceed the specified maximum allowed AV delay, at step 606 or 606', involves turning off the NAVH mode and returning to delivering baseline BiV pacing in response to determining that at least one of the plurality of different paced AV delays, that are each determined based on the intrinsic AV conduction interval and a different negative hysteresis delta, exceeds the specified maximum allowed AV delay. In such embodiments, the switching to baseline BiV pacing may occur because it is assumed that a calculated paced AV delay exceeding the maximum allowed AV delay was due to a patient experiencing AV block. More generally, the IMD 100 can be configured to switch from adaptive BiV fusion pacing to baseline BiV pacing whenever AV block is detected. Other variations are possible, and within the scope of the embodiments described herein. For example, if a paced AV delay that is calculated using Equation 1 exceeds the maximum allowed AV delay, then that paced AV delay can simply not be used, or can be limited to the maximum allowed AV delay.

Figure 7:
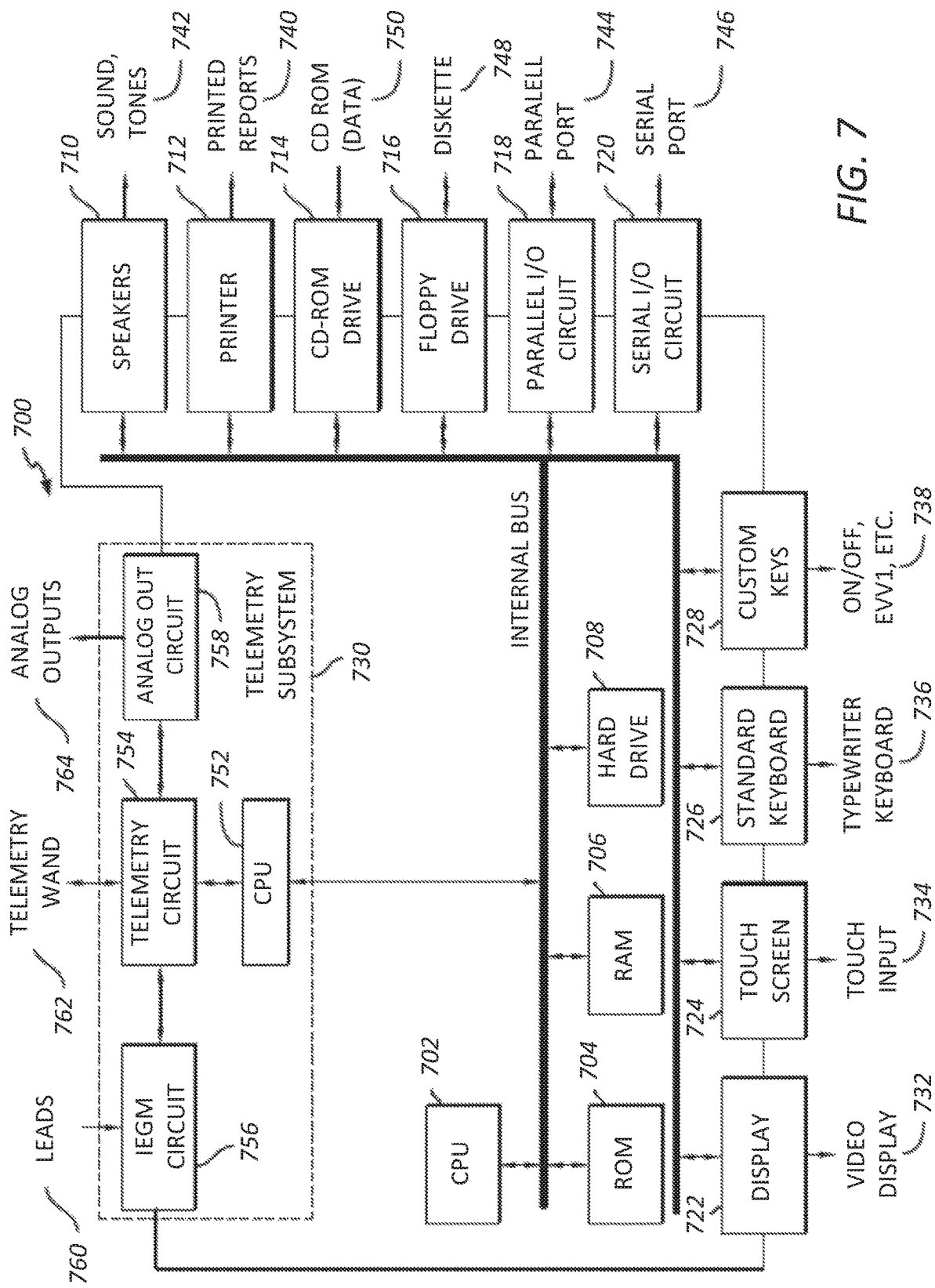
FIG. 7 illustrates a functional block diagram of an external device that is operated in accordance with the processes described herein.

FIG. 7 illustrates a functional block diagram of an external device 700 that is operated in accordance with the processes described herein and to interface with the implantable medical device 100 as shown in FIGS. 1 and 2 and described herein. The external device 700 may be the external programmer device 104 shown in FIG. 2. The external device 700 may take the form of a workstation, a portable computer, an IMD programmer, a PDA, a cell phone, and/or the like. The external device 700 includes an internal bus that connects/interfaces with a Central Processing Unit (CPU) 702, ROM 704, RAM 706, a hard drive 708, a speaker 710, a printer 712, a CD-ROM drive 714, a floppy drive 716, a parallel I/O circuit 718, a serial I/O circuit 720, a display 722, a touch screen 724, a standard keyboard 726, custom keys 728, and/or a telemetry subsystem 730. The internal bus is an address/data bus that transfers information between the various components described herein. The hard drive 708 may store operational programs as well as data, such as waveform templates, for the CRT pacing.

The CPU 702 includes a microprocessor, a micro-controller, and/or equivalent control circuitry, designed specifically to control interfacing with the external device 700 and with the IMD 100. The CPU 702 may include RAM or ROM memory, logic and timing circuitry, state machine circuitry, and/or I/O circuitry to interface with the IMD 100. The ROM 704, RAM 706 and/or hard drive 708 store program instructions that one executed by one or more processors (e.g., the CPU 702) to perform the operations described herein.

The display 722 may be connected to a video display 732. The display 722 displays various forms of information related to the processes described herein. The touch screen 724 may display graphic user information (GUI) relating to the IMD 100. For example, the GUI may provide a plurality of candidate parameters the user may select from to define the parameters for the negative hysteresis module 260. The touch screen 724 accepts a user's touch input 734 when selections are made. The keyboard 726 (e.g., a typewriter keyboard 736) allows a user to enter data to displayed fields, as well as interface with the telemetry subsystem 730. Furthermore, custom keys 728 turn on/off 738 (e.g., EVVI) the external device 700. The printer 712 prints copies of reports 740 for a physician to review or to be placed in a patient file, and speaker 710 provides an audible warning (e.g., sounds and tones 742) to the user. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a flash memory stick. The CD-ROM drive 714 accepts CD ROMs 750. The CD-ROM drive 714 optionally may include a DVD port capable of reading and/or writing DVDs.

The telemetry subsystem 730 includes a central processing unit (CPU) 752 in electrical communication with a telemetry circuit 754, which communicates with both an IEGM circuit 756 and an analog out circuit 758. The IEGM circuit 756 may be connected to leads 760. The IEGM circuit 756 is also connected to the implantable leads 120, 124 and 130 (shown in FIG. 1) to receive and process IEGM cardiac signals. Optionally, the IEGM cardiac signals sensed by the leads 120, 124 and 130 may be collected by the IMD 100 and then wirelessly transmitted to the telemetry subsystem 730 input of the external device 700.

The telemetry circuit 754 is connected to a telemetry wand 762. The analog out circuit 758 includes communication circuits to communicate with analog outputs 764. The external device 700 may wirelessly communicate with the IMD 100 and utilize protocols, such as Bluetooth, GSM, infrared wireless LANs, HIPERLAN, 3G, 4G, satellite, as well as circuit and packet data protocols, and the like. Alternatively, a hard-wired connection may be used to connect the external device 700 to the IMD 100.

The block diagrams of embodiments herein illustrate various blocks that may be labeled "module", "unit" and the like. It is to be understood that the modules, units, etc. represent circuits that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules, units, etc. may represent processing circuitry such as one or more field programmable gate array (FPGA), application specific integrated circuit (ASIC), or microprocessor. The modules, units, etc. in various embodiments may be configured to execute one or more algorithms to perform functions described herein. The one or more algorithms may include aspects of embodiments disclosed herein, whether or not expressly identified in a flowchart or a method.

The various methods as illustrated in the FIGS and described herein represent exemplary embodiments of methods. The methods may be implemented in software, hardware, or a combination thereof. In various embodiments of the methods, the order of certain steps may be changed, and various elements may be added, reordered, combined, omitted, modified, etc. For one example, step 606 may be performed before step 604 in FIG. 6A. For another example, step 606' may be performed before step 604 in FIG. 6B. Various steps of the method may be performed automatically (e.g., without being directly prompted by user input) and/or programmatically (e.g., according to program instructions). It is also possible that steps 606 and 608 are combined or otherwise performed in a manner that a new or updated intrinsic AV conduction interval is determined just before a new paced AV delay is to be tested, so that the new or updated intrinsic AV conduction interval is used to calculate (using Equation 1) the new paced AV delay to be tested.

Various modifications and changes may be made as would be obvious to a person skilled in the art having the benefit of this disclosure. It is intended to embrace all such modifications and changes and, accordingly, the above description is to be regarded in an illustrative rather than a restrictive sense.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for selectively delivering different types of bi-ventricular (BiV) pacing, comprising:
   (a) delivering baseline BiV pacing for a plurality of cardiac cycles and determining a corresponding baseline BiV efficacy score, wherein a predetermined atrio-ventricular (AV) delay is used for the baseline BiV pacing;
   (b) allowing for intrinsic AV conduction for a plurality of cardiac cycles and determining an intrinsic AV conduction interval and a corresponding intrinsic AV conduction efficacy score;
   (c) delivering BiV fusion pacing for a plurality of cardiac cycles and determining a corresponding negative AV hysteresis (NAVH) efficacy score, for each of a plurality of different paced AV delays, wherein each of the plurality of different paced AV delays is determined based on the intrinsic AV conduction interval and a different negative hysteresis delta;
   (d) based on results of steps (a), (b), and (c), either allowing for intrinsic AV conduction for a period of time, selecting and delivering the baseline BiV pacing for the period of time, or selecting and delivering BiV fusion pacing for the period of time using one of the plurality of different paced AV delays for which the corresponding NAVH efficacy score was determined.

2. The method of claim 1, further comprising:
   determining whether at least one premature ventricular contraction (PVC) occurs while the baseline BiV pacing is being delivered, or while the BiV fusion pacing is being delivered; and
   in response to determining that the at least one PVC occurs while the baseline BiV pacing is being delivered, the corresponding baseline BiV efficacy score is determined in a manner that is unaffected by the at least one PVC that occurs while the baseline BiV pacing is being delivered; or
   in response to determining that the at least one PVC occurs while the BiV fusion pacing is being delivered, determining at least one of the corresponding NAVH efficacy scores in a manner that is unaffected by the at least one PVC that occurs while the BiV fusion pacing is being delivered.

3. The method of claim 1, comprising wherein step (d) comprises:
   allowing for intrinsic AV conduction for the period of time in response to determining that the intrinsic AV conduction efficacy score is better than the baseline BiV efficacy score and better than all of the NAVH efficacy scores determined for the plurality of different paced AV delays;
   selecting and delivering the baseline BiV pacing for the period of time in response to determining that the baseline BiV efficacy score is better than the intrinsic AV conduction efficacy score and all of the NAVH efficacy scores determined for the plurality of different paced AV delays used during the BiV fusion pacing; or
   selecting and delivering BiV fusion pacing for the period of time, using one of the plurality of different paced AV delays for which the corresponding NAVH efficacy score was determined, in response to determining that the NAVH efficacy score corresponding to at least one of the plurality of different paced AV delays used during the BiV fusion pacing is better than the baseline BiV efficacy score and the intrinsic AV conduction efficacy score.

4. The method of claim 1, wherein each of the plurality of different paced AV delays is determined by subtracting a different negative hysteresis delta from the intrinsic AV conduction interval.

5. The method of claim 1, wherein step (d) includes determining whether the intrinsic AV conduction efficacy score is better than the baseline BiV efficacy score and better than all of the NAVH efficacy scores determined for the plurality of different paced AV delays, whether the baseline BiV efficacy score is better than the intrinsic AV conduction efficacy score and all of the NAVH efficacy scores determined for the plurality of different paced AV delays, or whether the NAVH efficacy score corresponding to at least one of the plurality of different paced AV delays is better than the intrinsic AV conduction efficacy score and the baseline BiV efficacy score.

6. The method of claim 1, wherein steps (a), (b), (c), and (d) are repeated from time to time and include:
   at a first point in time, determining that the baseline BiV efficacy score is better than all of the NAVH efficacy scores determined for the plurality of different paced AV delays used during the BiV fusion pacing, and in response thereto, the selecting and delivering at step (d) comprises selecting and delivering the baseline BiV pacing for a first period of time;
   at a second point in time, determining that the NAVH efficacy score corresponding to at least one of the plurality of different paced AV delays used during the BiV fusion pacing is better than the baseline BiV efficacy score, and in response thereto, the selecting and delivering at step (d) comprises selecting and delivering BiV fusion pacing for a second period of time using one of the plurality of different paced AV delays for which the corresponding efficacy score was determined to be better than the baseline BiV efficacy score; and
   at a third point in time, determining that the intrinsic AV conduction efficacy score is better than the baseline BiV efficacy score and better than all of the NAVH efficacy scores determined for the plurality of different paced AV delays used during the BiV fusion pacing, and in response thereto, at step (d) comprises allowing for intrinsic AV conduction for a third period of time.

7. The method of claim 1, further comprising:
   determining whether at least one premature ventricular contraction (PVC) occurs while the baseline BiV pacing is being delivered, while allowing for intrinsic AV conduction, and while the BiV fusion pacing is being delivered; and at least one of the following
   in response to determining that the at least one PVC occurs while the baseline BiV pacing is being delivered, the corresponding baseline BiV efficacy score is determined in a manner that is unaffected by the at least one PVC that occurs while the baseline BiV pacing is being delivered;
   in response to determining that the at least one PVC occurs while allowing for intrinsic AV conduction, the corresponding intrinsic AV conduction efficacy score is determined in a manner that is unaffected by the at least one PVC that occurs while allowing for intrinsic AV conduction; or
   in response to determining that the at least one PVC occurs while the BiV fusion pacing is being delivered, at least one of the corresponding NAVH efficacy scores is determined in a manner that is unaffected by the at least one PVC that occurs while the BiV fusion pacing is being delivered.

8. The method of claim 1, further comprising:
   for each of a plurality of different sets of BiV pacing parameters, using a sensor implanted in a pulmonary artery to obtain a corresponding measure of pulmonary artery pressure (PAP), and using one or more implanted electrodes to detect a QRS complex corresponding to each measure of PAP;
   identifying which of the measures of PAP is a best one of the measures of PAP; and
   saving, as a preferred QRS complex template, the detected QRS complex that corresponds to the best one of the measures of PAP;
   wherein the determining the intrinsic AV conduction efficacy score includes determining a measure of similarity between a QRS complex obtained while allowing intrinsic AV conduction and the saved preferred QRS complex template;
   wherein the determining the baseline BiV efficacy score includes determining a measure of similarity between a QRS complex obtained while delivering the baseline BiV pacing and the saved preferred QRS complex template; and
   wherein the determining the corresponding efficacy, for each of the plurality of different paced AV delays, includes determining a corresponding measure of similarity between a QRS complex obtained while pacing using one of the different paced AV delays and the saved preferred QRS complex template.

9. The method of claim 8, wherein:
the identifying which of the measures of PAP is the best one of the measures of PAP comprised identifying which of the measures of PAP is lowest; and
the saving, as the preferred QRS complex template, the detected QRS complex that corresponds to the best one of the measures of PAP, comprises saving, as the preferred QRS complex template, the detected QRS complex that corresponds to the measure of PAP that is the lowest.

10. The method of claim 1, wherein:
each efficacy score is based on at least one of QRS width or QRS morphology.

11. A system, comprising:
a first lead comprising at least one electrode configured to be implanted in a left ventricle;

a second lead comprising at least one electrode configured to be implanted in a right ventricle;

at least one pulse generator each of which is coupleable to at least one of the first and second leads and each of which is configured to deliver cardiac stimulation pulses to pacing sites using at least one of the electrodes;

at least one sensing circuit each of which is configured to obtain at least one signal indicative of electrical activity of a patient's heart;

at least one processor for use in specifying an atrioventricular (AV) pacing delay used for bi-ventricular (BiV) pacing and specifying which of the electrodes are used for pacing;

wherein the system is configured to use the leads, the at least one pulse generator, the at least one sensing circuit, and the at least one processor, to deliver baseline BiV pacing for a plurality of cardiac cycles and determine a corresponding baseline BiV efficacy score, wherein a predetermined AV delay is used for the baseline BiV pacing;

allow for intrinsic AV conduction for a plurality of cardiac cycles and determine an intrinsic AV conduction interval and a corresponding intrinsic AV conduction efficacy score;

deliver BiV fusion pacing for a plurality of cardiac cycles and determine a corresponding negative AV hysteresis (NAVH) efficacy score, for each of a plurality of different paced AV delays, wherein each of the plurality of different paced AV delays is determined based on the intrinsic AV conduction interval and a different negative hysteresis delta;

select and deliver baseline BiV pacing for a period of time if the baseline BiV efficacy score is better than the intrinsic AV conduction score and all of the NAVH efficacy scores corresponding the plurality of different paced AV delays used during the BiV fusion pacing;

select and deliver BiV fusion pacing for the period of time, using one of the plurality of different paced AV delays for which a corresponding NAVH efficacy score was determined, if the NAVH efficacy score corresponding to at least one of the plurality of different paced AV delays used during the BiV fusion pacing is better than the baseline BiV efficacy score and the intrinsic AV conduction score; and allow for intrinsic AV conduction for the period of time, if the intrinsic AV conduction efficacy score is better than the baseline BiV efficacy score and better than all of the NAVH efficacy scores determined for the plurality of different paced AV delays used during the BiV fusion pacing.

12. The system of claim 11, wherein the at least one processor is also configured to:

determine whether at least one premature ventricular contraction (PVC) occurs while the baseline BiV pacing is being delivered, while allowing for intrinsic AV conduction, or while the BiV fusion pacing is being delivered; and in response to determining that the at least one PVC occurs while the baseline BiV pacing is being delivered, determine the corresponding baseline BiV efficacy score in a manner that is unaffected by the at least one PVC that occurs while the baseline BiV pacing is being delivered;

in response to determining that the at least one PVC occurs while allowing for intrinsic AV conduction, determine the intrinsic AV conduction interval in a manner that is unaffected by the at least one PVC that occurs while allowing for intrinsic AV conduction; or in response to determining that the at least one PVC occurs while the BiV fusion pacing is being delivered, determine at least one of the corresponding NAVH efficacy scores in a manner that is unaffected by the at least one PVC that occurs while the BiV fusion pacing is being delivered.

13. The system of claim 11, further comprising:

a sensor configured to be implanted in a pulmonary artery; and wherein the at least one processor is also configured to determine the corresponding intrinsic AV conduction efficacy score by using the sensor to obtain a corresponding measure of pulmonary artery pressure (PAP) while allowing for intrinsic AV conduction;

determine the corresponding baseline BiV efficacy score by using the sensor to obtain a corresponding measure of PAP while baseline BiV pacing is being delivered; and determine the corresponding NAVH efficacy score, for each of the plurality of different paced AV delays, by using the sensor to obtain a corresponding measure of PAP for each of the plurality of different paced AV delays.

14. The system of claim 11, further comprising:

a sensor configured to be implanted in a pulmonary artery; and wherein the system is also configured to use the leads, the at least one pulse generator, the at least one sensing circuit, the at least one processor, and the sensor to obtain a corresponding measure of pulmonary artery pressure (PAP), and detect a QRS complex corresponding to each measure of PAP, for each of a plurality of different sets of BiV pacing parameters;

identify which of the measures of PAP is a best one of the measures of PAP; and save, as a preferred QRS complex template, the detected QRS complex that corresponds to the best one of the measures of PAP; and wherein the at least one processor is also configured to determine the baseline BiV efficacy score by determining a measure of similarity between a QRS complex obtained while the baseline BiV pacing is being delivered and the saved preferred QRS complex template;

determine the corresponding NAVH efficacy score, for each of the plurality of different paced AV delays, by determining a corresponding measure of similarity between a QRS complex obtained while pacing using one of the different paced AV delays and the saved preferred QRS complex template; and determine the intrinsic AV conduction efficacy score by determining a measure of similarity between a QRS complex obtained while allowing intrinsic AV conduction and the saved preferred QRS complex template.

15. The system of claim 14, wherein the at least one processor is configured to:

identify a lowest one of the measures of PAP as the best one of the measures of PAP; and save, as the preferred QRS complex template, the detected QRS complex that corresponds to the lowest one of the measures of PAP.

16. The system of claim 11, wherein:
each efficacy score is based on at least one of QRS width or QRS morphology.

17. The system of claim 11, wherein that at least one processor is configured to ensure that none of the paced AV delays exceed a specified maximum allowed AV delay.

18. The system of claim 11, wherein at least one of the different negative hysteresis deltas, used to determine the plurality of different paced AV delays, is stored in memory of the system.

19. The system of claim 11, wherein the different negative hysteresis deltas are between ten and one hundred twenty milliseconds.

20. The method of claim 2, wherein a said efficacy score is determined in a manner that is unaffected by the at least one PVC by ignoring or excluding a measurement, used to determine the said efficacy score, that is associated with at least one cardiac cycle in which the at least one PVC occurs.

* * * * *